United States Patent
Liu et al.

(10) Patent No.: US 6,534,269 B2
(45) Date of Patent: Mar. 18, 2003

(54) PYROPHOSPHOROLYSIS ACTIVATED POLYMERIZATION (PAP): APPLICATION TO ALLELE-SPECIFIC AMPLIFICATION AND NUCLEIC ACID SEQUENCE DETERMINATION

(75) Inventors: Qiang Liu, Upland, CA (US); Steve S. Sommer, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/789,556

(22) Filed: Feb. 22, 2001

(65) Prior Publication Data

US 2002/0127554 A1 Sep. 12, 2002

Related U.S. Application Data

(60) Provisional application No. 60/184,315, filed on Feb. 23, 2000, provisional application No. 60/187,035, filed on Mar. 6, 2000, and provisional application No. 60/237,180, filed on Oct. 3, 2000.

(51) Int. Cl.[7] .............................. C12Q 1/68; C12P 19/34
(52) U.S. Cl. ........................... 435/6; 435/91.1; 435/91.2
(58) Field of Search ........................... 435/6, 91.1, 91.2

(56) References Cited

U.S. PATENT DOCUMENTS

| | | | |
|---|---|---|---|
| 5,302,509 | A | 4/1994 | Cheeseman |
| 6,159,693 | A * | 12/2000 | Shultz et al. ................... 435/6 |
| 6,235,480 | B1 * | 5/2001 | Shultz et al. ................... 435/6 |
| 6,335,162 | B1 * | 1/2002 | Shultz et al. ................... 435/6 |

FOREIGN PATENT DOCUMENTS

| | | |
|---|---|---|
| EP | 0 892 058 | 1/1999 |

OTHER PUBLICATIONS

Liu et al., Am. J. Hum. Genet. 67 (4 Supplement 2), 267 (Oct. 2000).*

Liu, Q. et al., "Pyrophoshorolysis–Activated Polymerization (PAP): Application to Allele–Specific Amplification," *Biotechniques* 29: 1072–1083, 2000.

(List continued on next page.)

*Primary Examiner*—Kenneth R. Horlick
(74) *Attorney, Agent, or Firm*—Rothwell, Figg, Ernst & Manbeck

(57) ABSTRACT

A novel method of pyrophosphorolysis activated polymerization (PAP) has been developed. In PAP, pyrophosphorolysis and polymerization by DNA polymerase are coupled serially for each amplification by using an activatable oligonucleotide P* that has a non-extendable 3'-deoxynucleotide at its 3' terminus. PAP can be applied for exponential amplification or for linear amplification. PAP can be applied to amplification of a rare allele in admixture with one or more wild type alleles by using an activatable oligonucleotide P* that is an exact match at its 3' end for the rare allele but has a mismatch at or near its 3' terminus for the wild type allele. PAP is inhibited by a mismatch in the 3' specific subsequence as far as 16 nucleotides away from the 3' terminus. PAP can greatly increase the specificity of detection of an extremely rare mutant allele in the presence of the wild type allele. Specificity results from both pyrophosphorolysis and polymerization since significant nonspecific amplification requires the combination of mismatch pyrophosphorolysis and misincorporation by the DNA polymerase, an extremely rare event. Using genetically engineered DNA polymerases greatly improves the efficiency of PAP.

98 Claims, 12 Drawing Sheets

OTHER PUBLICATIONS

BI, W. and Stambrook, P.J., "Detection of known mutation by proof–reading PCR," *Nucleic Acids Res*, 1998, 26:3073–3075.

Meyer, P.R. et al., "Unblocking of chain–terminated pirmer by HIV–1 reverse trancriptase through a nucleotide–dependent mechanism," *Proc Natl Sci USA*, 1998, 95:13471–13476.

Steve S. Sommer et al., "PCR Amplification of Specific Alles (PASA) is a General Method for Rapidly Detecting Known Single–Base Changes," Biotechniques 12(1):82–87, 1992.

Stanley Tabor et al., "DNA Sequence Analysis with a Modified Bacteriophage T7 DNA Polymerase," The Journal of Biological Chemistry 265(14):8322–8328, May 15, 1990.

* cited by examiner

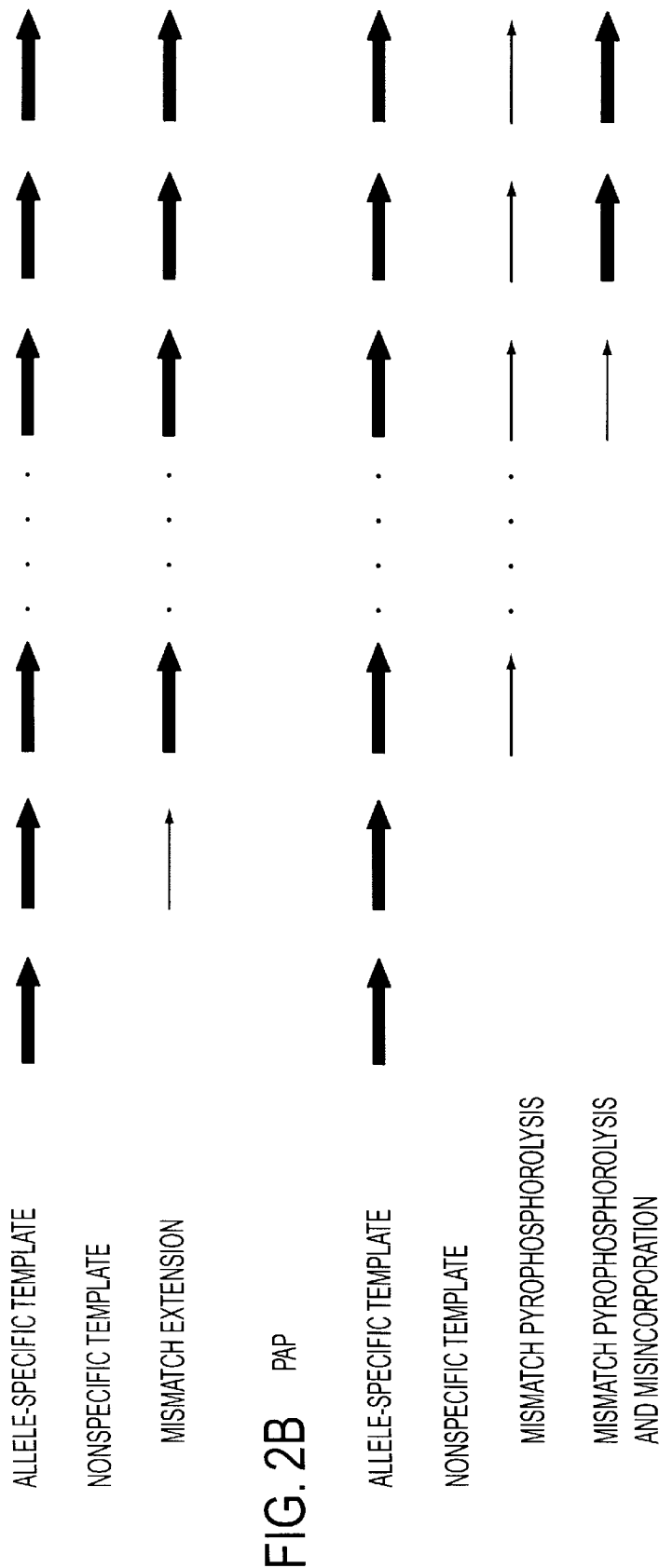

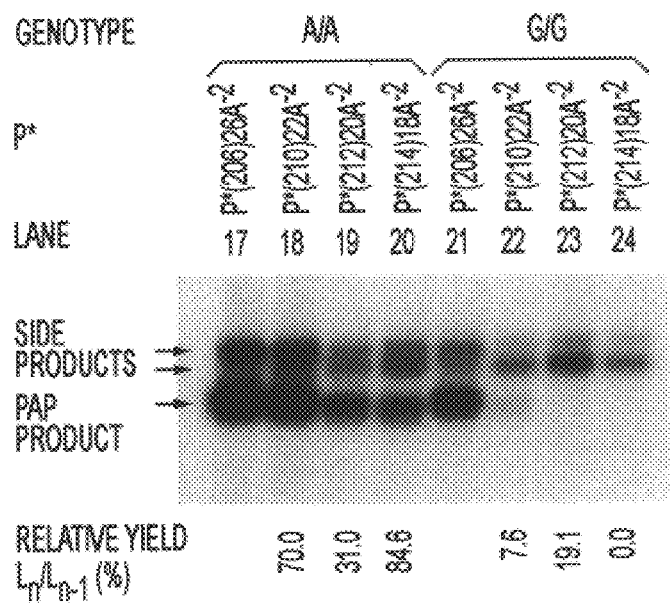
FIG. 7C
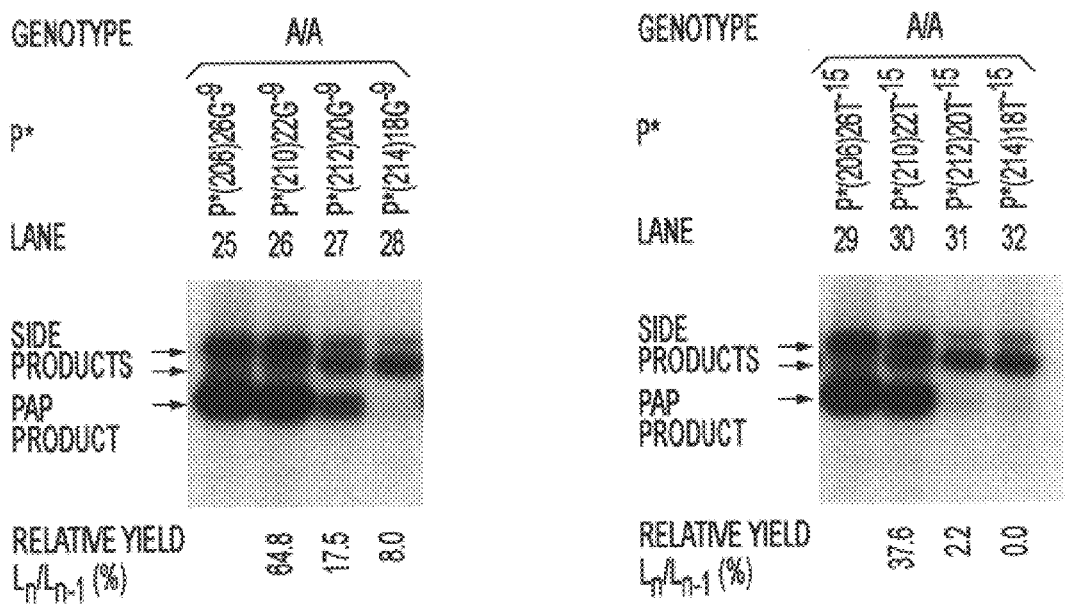
FIG. 7D
FIG. 7E

PYROPHOSPHOROLYSIS ACTIVATED POLYMERIZATION (PAP): APPLICATION TO ALLELE-SPECIFIC AMPLIFICATION AND NUCLEIC ACID SEQUENCE DETERMINATION

CROSS-REFERENCE TO RELATED APPLICATIONS

The present application is related to U.S. provisional patent application Serial Nos. 60/184,315 filed on Feb. 23, 2000, Ser. No. 60/187,035 filed on Mar. 6, 2000 and Ser. No. 60/237,180 filed Oct. 3, 2000.

BACKGROUND OF THE INVENTION

This invention relates to nucleic acid polymerization and amplification. In particular, it relates to a novel and general method for nucleic acid amplification, in which pyrophosphorolysis and polymerization are serially-coupled. The method has been adapted for allele-specific amplification and can greatly increase the specificity to detect an extremely rare allele in the presence of wild type alleles. We refer to the method as pyrophosphorolysis activated polymerization (PAP).

The publications and other materials used herein to illuminate the background of the invention or provide additional details respecting the practice, are incorporated by reference, and for convenience are respectively grouped in the appended Lists of References.

A method of detecting one mutant allele in $10^6$–$10^9$ wild type alleles would be advantageous for many applications including detecting minimal residual disease (rare remaining cancer cells during remission, especially mutations in the p53 gene or other tumor suppressor genes previously identified within the tumors) and measurement of mutation load (the frequency of specific somatic mutations present in normal tissues, such as blood or urine). Individuals with a high mutation load may be at increased risk for cancer to either environmental exposure or endogenous defects in any of hundreds of genes necessary to maintain the integrity of the genome. For those individuals found to have a high mutation load, clues to etiology can be obtained by defining the mutation pattern.

Multiple methods for detecting mutations present in less than 10% of cells (i.e. rare alleles) have been developed including PCR amplification of specific alleles (PASA), PNA clamping blocker PCR, allele specific competitive blocker PCR, MAMA, and RFLP/PCR (1). These methods: i) amplify the rare allele selectively, ii) destroy the abundant wild type allele, or iii) spatially separate the rare allele from the wild type allele. RFLP/PCR has been reported to have the highest specificity of $10^{-8}$ (2), but in our hands the specificity has been $10^{-3}$ to $10^{-4}$ (3). Methods that selectively amplify the rare allele include PASA, which routinely has a specificity of less than or equal to 1 part in 40 (4).

DNA polymerases, which are critical to DNA amplification, catalyze some or all of the following reactions: i) polymerization of deoxynucleotide triphosphates; ii) pyrophosphorolysis of duplexes of DNA in the presence of pyrophosphate ($PP_i$); iii) 3'-5' exonuclease activity and iv) 5'-3' exonuclease activity (5, 6). For Taq and Tfl DNA polymerases, the polymerization and 5'-3' exonuclease activity have been reported (7–9). For T7 Sequenase™ DNA polymerases, pyrophosphorolysis can lead to the degradation of specific dideoxynucleotide-terminated segments in Sanger sequencing reaction (10, 11).

There are many DNA sequencing methods and their variants, such as the Sanger sequencing using dideoxy termination and denaturing gel electrophoresis (27), Maxam-Gilber sequencing using chemical cleavage and denaturing gel electrophoresis (28), pyro-sequencing detection pyrophosphate (PPi) released during the DNA polymerase reaction (29), and sequencing by hybridization (SBH) using oligonucleotides (30–35).

Herein, we describe pyrophosphorolysis activated polymerization (PAP), an approach which has the potential to enhance dramatically the specificity of PASA. We also describe a novel method of DNA sequence determination by PAP.

SUMMARY OF THE INVENTION

The invention is a pyrophosphorolysis activated polymerization (PAP) method of synthesizing a desired nucleic acid strand on a nucleic acid template strand. The method comprises the following steps carried out serially.

(a) Annealing to the template strand a complementary activatable oligonucleotide P*. This activatable oligonucleotide has a non-extendable 3'-deoxynucleotide at its 3' terminus. It has no nucleotides at or near its 3' terminus that mismatch the corresponding nucleotides on the template strand. Therefore, the terminal 3'-deoxynucleotide is hybridized to the template strand when the oligonucleotide P* is annealed.

(b) Pyrophosphorolyzing the annealed activatable oligonucleotide P* with pyrophosphate and an enzyme that has pyrophosphorolysis activity. This activates the oligonucleotide P* by removal of the hybridized terminal 3'-deoxynucleotide.

(c) Polymerizing by extending the activated oligonucleotide P* on the template strand in presence of four nucleoside triphosphates and a nucleic acid polymerase to synthesize the desired nucleic acid strand.

The PAP method can be applied to amplify a desired nucleic acid strand by the following additional steps.

(d) Separating the desired nucleic acid strand of step (c) from the template strand, and (e) Repeating steps (a)–(d) until a desired level of amplification of the desired nucleic acid strand is achieved.

In a preferred aspect, the PAP method as described above is applied to allele-specific amplification. In this application, the nucleic acid template strand is a sense or antisense strand of one allele and is present in admixture with the corresponding (sense or antisense) nucleic acid strand of the second allele (the allelelic strand). The activatable oligonucleotide P* has at least one nucleotide at or near its 3' terminus that mismatches the corresponding nucleotide of the allelic strand. Because of the mismatch, in step (a) of the PAP method the terminal 3'-deoxynucleotide of oligonucleotide P* is not hybridized to the allelelic strand. In step (b) the pyrophosphorolysis does not substantially remove the non-hybridized terminal 3'-deoxynucleotide from the activatable oligonucleotide P* annealed to the allelic strand. In step (c) the oligonucleotide P* is not substantially extended by polymerization on the allelic strand. As a result, the desired nucleic acid strand synthesized on the template strand is amplified preferentially over any nucleic acid strand synthesized on the allelelic strand.

The PAP method can be used to amplify either RNA or DNA. When used to amplify DNA, the activatable oligonucleotide P* is a 2'-deoxyoligonucleotide, the terminal deoxynucleotide is a 2',3'-dideoxynucleotide, the four nucleoside triphosphates are 2'-deoxynucleoside triphosphates, and the nucleic acid polymerase is a DNA polymerase. The DNA polymerase used in step (c) can also be the enzyme having pyrophosphorolysis activity used in step (b). Preferred DNA polymerases having pyrophosphorolysis activity are thermostable Tfl, Taq, and genetically engineered DNA polymerases, such as AmpliTaqFs and ThermoSequenase™. These genetically engineered DNA polymerases have the mutation F667Y in their active sites and elimination of 5'-3' exonuclease activity. The use of genetically engineered DNA polymerases, such as AmpliTaqFs and ThermoSequenase™, greatly improves the efficiency of PAP.

Amplification by the PAP method can be linear or exponential. Linear amplification is obtained when the activatable oligonucleotide P* is the only complementary oligonucleotide used. Exponential amplification is obtained when a second oligonucleotide is present that is complementary to the desired nucleic acid strand. The activatable oligonucleotide P* and the second oligonucleotide flank the region that is targeted for amplification. In step (a) the second oligonucleotide anneals to the separated desired nucleic acid strand product of step (d). In step (c) polymerization extends the second oligonucleotide on the desired nucleic acid strand to synthesize a copy of the nucleic acid template strand. In step (d) the synthesized nucleic acid template strand is separated from the desired nucleic acid strand. Steps (a) through (d) are repeated until the desired level exponential amplification has been achieved.

In the PAP method, a mismatch between the activatable oligonucleotide P* and the template strand results in no amplification, if the mismatch occurs in the 3' specific subsequence of P* at the 3' terminus of P* or within 16 nucleotides of the 3' terminus of P*. This lack of amplification for such mismatches in the 3' specific subsequence of P* provides four billion different and specific oligonucleotides with one base substitution resolution.

In a preferred aspect, the PAP method is used for exponential amplification of a rare, mutant allele in a mixture containing one or more wild-type alleles. Strands of the alleles are separated to provide single-stranded DNA, then the following steps are carried out serially.

(a) Annealing to the sense or antisense strands of each allele a complementary activatable 2'-deoxyoligonucleotide P* that has a non-extendable 2',3'-deoxynucleotide at its 3' terminus. P* has no 2'-deoxynucleotides at or near its 3' terminus that mismatch the corresponding 2'-deoxynucleotides on the mutant strand, but has at least one 2'-deoxynucleotide at or near its 3' terminus that mismatches the corresponding 2'-deoxynucleotide on the wild type stand. Consequently, the terminal 2',3'-deoxynucleotide is hybridized to the mutant strand but not to the wild-type strand when the oligonucleotide P* is annealed. Simultaneously, a second 2'-deoxyoligonucleotide that is complementary to the anti-parallel strands of each allele is annealed to the anti-parallel strands. The activatable 2'-deoxyoligonucleotide P* and the second 2'-deoxyoligonucleotide flank the region of the gene to be amplified.

(b) Pyrophosphorolyzing the activatable 2'-deoxyoligonucleotide P* that is annealed to a mutant strand with pyrophosphate and an enzyme that has pyrophosphorolysis activity. This activates the 2'-deoxyoligonucleotide P* that is annealed to the mutant strand by removal of the hybridized terminal 2',3'-deoxynucleotide. It does not substantially activate the 2'-deoxyoligonucleotide P* that is annealed to the mutant strand because the non-hybridized terminal 2',3'-deoxynucleotide is not substantially removed by the pyrophosporolysis.

(c) Polymerizing by extending the activated oligonucleotide P* on the mutant strand in presence of four nucleoside triphosphates and a DNA polymerase and simultaneously extending the second 2'-deoxyoligonucleotide on both mutant and wild-type anti-parallel strands.

(d) Separating the extension products of step (c);

(e) Repeating steps (a)–(d) until the desired level of exponential amplification of the mutant allele has been achieved.

The activatable 2'-deoxyoligonucleotide P* is annealed to the antisense strands of the alleles and the second 2'-deoxyoligonucleotide is annealed to the sense strands, or vice versa.

Steps (a) to (c) of PAP can be conducted sequentially as two or more temperature stages on a thermocycler, or they can be conducted as one temperature stage on a thermocycler.

Nucleoside triphosphates and 2'-deoxynucleoside triphosphates or their chemically modified versions may be used as substrates for multiple-nucleotide extension by PAP, i.e., when one nucleotide is incorporated the extending strand can be further extended. 2',3'-dideoxynucleoside triphosphates or their chemically modified versions which are terminators for further extension may be used for single-nucleotide extension. 2',3' dideoxynucleoside triphosphates may be labeled with radioactivity or fluorescence dye for differentiation from the 3' terminal dideoxynucleotide of oligonucleotide P*. Mixtures of nucleoside triphosphates or 2'-deoxynucleotide triphosphates and 2',3'-dideoxynucleoside triphosphates may also be used.

PAP can be used in a novel method of DNA sequence determination. In PAP, pyrophosphorolysis and polymerization by DNA polymerase are coupled serially by using P*, a 3' dideoxy terminal oligonucleotide. This principle is based on the specificity of PAP and in turn on the base pairing specificity of the 3' specific subsequence. This property of the 3' specific subsequence can be applied to scan for unknown sequence variants, to determine de novo DNA sequence, to compare two DNA sequences, and to monitor gene expression profiling in large scale. A P* array is possible in these methods. That is, each of the P*s can be immobilized at an individual dot or a two dimensional solid support, thus allowing all the PAP reactions to be processed in parallel.

Thus in one aspect, the PAP method is used for scanning unknown sequence variants in a nucleic acid sequence or for resequencing of a predetermined sequence in a nucleic acid by carrying out the following steps serially.

(a) Mixing under hybridization conditions a template strand of the nucleic acid with multiple sets of four activatable oligonucleotides P* which are sufficiently complementary to the template strand to hybridize therewith. Within each set the oligonucleotides P* differ, from each other in having a different 3'-terminal non-extendable nucleotide, so that the 3' terminal non-extendable nucleotide is hybridized to the template strand if the template strand is complementary to the 3' terminal non-extendable nucleotide. The number of sets correspond to the number of nucleotides in the sequence.

(b) Treating the resulting duplexes with pyrophosphate and an enzyme that has pyrophosphorolysis activity to activate by pyrophosphorolysis only those oligonucleotides P* which have a 3' terminal non-extendable nucleotide that is hybridized to the template strand.

(c) Polymerizing by extending the activated oligonucleotides P* on the template strand in presence of four nucleoside triphosphates and a nucleic acid polymerase.

(d) Separating the nucleic acid strands synthesized in step (c) from the template strand.

(e) Repeating steps (a)–(d) until a desired level of amplification is achieved, and (f) Arranging the nucleic acid sequence in order by analyzing overlaps of oligonuclotides P* that produced amplifications.

In a second aspect, the PAP method is used for determining de novo the sequence of a nucleic acid by carrying out the following steps serially.

(a) Mixing under hybridization conditions a template strand of the nucleic acid with multiple activatable oligonucleotides P*. All of the oligonucleotides P* have the same number n of nucleotides as the template and constitute collectively all possible sequences having n nucleotides. All of the oligonucleotides P* have a non-extendable nucleotide at the 3' terminus. Any oligonucleotides P* that are sufficiently complementary will hybridize to the template strand. The 3' terminal non-extendable nucleotide will hybridize to the template strand only if the template strand is complementary at the position corresponding to the 3' terminus.

(b) Treating the resulting duplexes with pyrophosphate and an enzyme that has pyrophosphorolysis activity to activate only those hybridized oligonucleotides P* which have a 3' terminal non-extendable nucleotide that is hybridized to the template strand, by pyrophosphorolysis of those hybridized 3' terminal non-extendable nucleotides.

(c) Polymerizing by extending the activated oligonucleotides P* on the template strand in presence of four nucleoside triphosphates and a nucleic acid polymerase.

(d) Separating the nucleic acid strands synthesized in step (c) from the template strand.

(e) Repeating steps (a)–(d) until a desired level of amplification has been achieved, and (f) Determining the sequence of oligonucleotides P* that produced amplifications, then arranging the nucleic acid sequence in order by analyzing overlaps of these oligonucleotides.

BRIEF DESCRIPTION OF THE FIGURES

FIGS. 2A–2B are diagrams illustrating enhanced specificity of PAP relative to PASA.

FIGS. 7A–7E are autoradiograms showing the results of electrophoresis of samples obtained in Example 2 below.

DETAILED DESCRIPTION OF THE INVENTION

The invention can be understood from the following Examples, which illustrate that PAP can be used to identify a known mutation in a polymorphic site within the human $D_1$ dopamine receptor gene. The effects of the dideoxyoligonucleotide sequences, DNA polymerases, $PP_i$ concentrations, allele-specific templates, pH, and dNTP concentrations were examined. The experiments reported in the Examples were conducted for proof of principle. The following examples are offered by way of illustration and are not intended to limit the invention in any manner. Standard techniques well known in the art or the techniques specifically described therein were utilized.

EXAMPLE 1

Preparation of Template by PCR

Figure 1A:
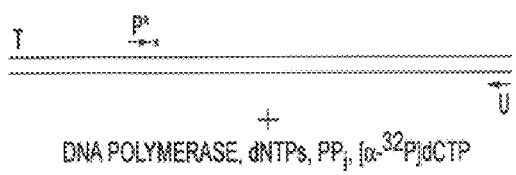
FIGS. 1A and 1B are a schematic illustrating use of PAP to detect the G allele at nucleotide 229 of the $D_1$ dopamine receptor gene. The procedure is described in detail in Example 1 below.

A 640-bp region of the human $D_1$ dopamine receptor gene was amplified by PCR with two primers (T=5' GAC CTG CAG CAA GGG AGT CAG AAG 3' (SEQ ID NO:1) and U=5' TCA TAC CGG AAA GGG CTG GAG ATA 3' (SEQ ID NO:2)) (FIG. 1A). The TU:UT duplexed product spans nucleotides 33 to 672 in GenBank X55760 and the G+C content is 55.3%. A common A to G polymorphism is located at nucleotide 229, resulting in three genotypes of G/G, A/A and G/A (12). The PCR mixture contains a volume of 50 µl: 50 mM KCl, 10 mM Tris/HCl, pH 8.3, 1.5 mM $MgCl_2$, 200 µM each of the four dNTPs (Boehringer Mannheim), 0.1 µM of each primer, 2% DMSO, 1 U of Taq DNA polymerase (Boehringer Mannheim) and 250 ng of genomic DNA from G/G homozygote, A/A homozygote or G/A heterozygotes. Cycling conditions included: denaturation at 95° C. for 15 seconds, annealing at 55° C. for 30 seconds, and elongation at 72° C. one minute, for a total of 35 cycles (Perkin Elmer GeneAmp PCR system 9600). The PCR product was purified from primers and other small molecules by approximately 10,000-fold by three times of retention on a Centricon® 100 microconcentrator (Amicon). The amount of recovered PCR product was determined by UV absorbance at 260 nm.

Synthesis of P* by Adding a 3'-dideoxynucleotide

The deoxynucleotide oligonucleotide was synthesized by Perseptive Biosystems 8909 Synthesizer (Framinsham) and purified by oligopure cartridges (Hamilton) in the City of Hope DNA/RNA Chemistry Laboratory. The 3' terminal dideoxynucleotide was added by terminal transferase. The mixture contained a total volume of 40 µl: 200 mM potassium cacodylate, 25 mM Tris/HCl (pH 6.6 at 25 ° C.), 2.5 mM $CoCl_2$, 0.25 mg/ml of BSA, 4000 pM of the oligonucleotide, 2.5 mM 2'3'-ddNTP (the molar ratio of the 3'-OH terminus to ddNTP was 1:25) Boehringer Mannheim), 125 U of terminal transferase (Boehringer Mannheim). The reaction was incubated at 37° C. for 1 hour and then stopped by adding EDTA at 5 mM final concentration. After desalting by using butanol, the dideoxyoligonucleotide was purified by preparative 7M urea/20% polyacrylamide gel electrophoresis in TBE buffer (90 mM Tris/borate, 1 mM EDTA, pH 8.3) (25). The amount of the recovered P* was determined by UV absorbance at 260 nm.

Since small amounts of unterminated oligonucleotide would result in nonspecificity of pyrophosphorolysis, each dideoxyoligonucleotide was $^{32}$P-labeled at the 5' terminus by T4 polynucleotide kinase and then was electrophoresed through a 7M urea/20% polyacrylamide gel. Only P* products were visible even when the gel was overexposed (data not shown). It is estimated that more than 99.99% of P* contained a dideoxynucleotide at the 3' terminus.

Pyrophosphorolysis Activated Polymerization

A 469-bp region within the TU:UT duplexed template was amplified by PAP with oligonucleotides P* and U, or with only one P* (Table 1 and FIG. 1A). The PU:UP duplexed product corresponds to nucleotides 204 to 672 in GenBank X55760 and the G+C content is 55.6%. Unless stated, the PAP reaction mixture contained a total volume of 25 μl for Tfl DNA polymerase: 75 mM KCl, 20 mM Tris/HCl (pH 7.4), 1.5 mM MgCl$_2$, 40 μM each of the four DNTPs (dATP, dTTP, dGTP and dCTP), 0.2 μM P*, 0.05 μM U oligonucleotide, 300 μM Na$_4$PP$_i$ (the 20 MM stock solution was adjusted by HCl to pH 8.0), 1 μCi of [α-$^{32}$P]-dCTP (3000Ci/nmole, Amersham), 1 U of Tfl DNA polymerase (Promega) and 2 ng of TU:UT. For Taq DNA polymerase, the reaction mixture was the same except for 50 mM Kcl, 10 mM Tris/HCl (pH 7.4), 2.0 mM MgCl$_2$ and 1 U of Taq DNA polymerase (Boehringer Mannheim). The mixtures of PCR and other controls were the same except for the primers added. Cycling conditions included: 94° C. for 15 seconds, 55° C. for one minute, ramping to 72° C. for one minute and 72° C. for two minutes, for a total of 15 cycles.

TABLE 1

Oligonucleotides used in PAP (SEQ ID NO: 3)

Template  5' . . . AATCTGACTGACCCCTATTCCCTGCTT G̲ GGAAC . . . 3'
                                                    A

| Name | Olgonucleotide sequence 5'-3' (SEQ ID NO:) | Purpose |
|---|---|---|
| D$_1$ | ACTGACCCCTATTCCCTGCTT$^b$ (4) | Control |
| D$_1$G*$^a$ | ACTGACCCCTATTCCCTGCTTG*$^b$ (5) | 3' ddG and G allele specificity co-localized |
| D$_2$G* | ACTGACCCCTATTCCCTGCTTGG* (6) | G allele specificity 5' to ddG |
| D$_3$G* | ACTGACCCCTATTCCCTGCTTGGG* (7) | G allele specificity 5' to ddG |
| D$_4$G* | ACTGACCCCTATTCCCTGCTTGGGG* (8) | 3' ddG mismatches template |
| D$_5$G* | TCTGACTGACCCCTATTCCCTGCTTG* (9) | D$_1$G*, with 5' extended bases |
| D$_6$A* | TGACTGACCCCTATTCCCTGCTTA* (10) | 3'ddA and A allele-specificity co-localized |
| U | TCATACCGGAAAGGGCTGGAGATA (11) | Upstream oligonucleotide |

| | 3' terminal nucleotide$^c$ | | Allele-specific nucleotide$^d$ | | | | Amplification$^f$ | |
|---|---|---|---|---|---|---|---|---|
| Name | Type | Match | From 3' terminus Type | Size (bp) | (base) | T$_m$ (° C.)$^e$ | G Allele | A Allele |
| D$_1$ | dT | Yes | — | +1 | 21 | 64 | Yes | Yes |
| D$_1$G* | ddG | Yes | G | 0 | 22 | 68 | No | No |
| D$_2$G* | ddG | Yes | G | -1 | 23 | 72 | No | No |
| D$_3$G* | ddG | Yes | G | -2 | 24 | 76 | Yes | No |
| D$_4$G* | ddG | No | G | -3 | 25 | 80 | No | No |
| D$_5$G* | ddG | Yes | G | 0 | 26 | 80 | Yes | No |
| D$_6$A* | ddA | Yes | A | 0 | 24 | 72 | No | No |
| U | dA | Yes | — | — | 24 | 72 | Yes | Yes |

$^a$D$_1$G* was produced by adding a G dideoxynucleotide to the 3' terminus of the D$_1$, * = a dideoxynucleotide at the 3' terminus.
$^b$The T means the 3' terminus is T deoxynucleotide and G* means the 3' terminus is G dideoxynucleotide. The bold capital G and A are the G and A bases corresponding to G and A alleles, respectively. The first base at the 5' terminus corresponds to nucleotide 208 in Genbank X55760.
$^c$The 3' terminal base is a deoxynucleotide or dideoxynucleotide, and creates a match (Yes) or a mismatch (No) with the corresponding base on the complementary strand of the template.

TABLE 1-continued

Oligonucleotides used in PAP

[d]The allele-specific nucleotide is G or A and its distance to the 3' terminus is assigned: 0 = at the 3' terminus +1 = one base downstream from the 3' terminus, -1 = one base upstream from the 3' terminus, -2 = two bases upstream from the 3' terminus, and -3 = three bases upstream from the 3' terminus.
[e]The $T_m$ for oligonucleotides was estimated to be 4° C. X(G + C) + 2° C. X(T + A) at 1M NaCl (26).
[f]The amplification with U and one P* or with only one P*.

The reaction was electrophoresed through a standard 2% agarose gel. The gel was stained with ethidium bromide for UV photography by a CCD camera (Bio-Rad Gel Doc 1000), dried and subjected to Kodak X-OMA™ AR film for autoradiography.

Restriction Digestion

Each of the three restriction endonucleases of AciI (5'C▲CGC3'/3'GGC▼G5') EaeI (5'Py▲GGCCPu3'/3'PuCCGG▼Py5') and Eco0109I (5'PuG▲GNCCPy3'/3'PyCCNG▼GPu5') has a restriction site within the PU:UP duplex. The G/G alleles were amplified by PAP with $D_5G^*$ and U; PCR amplification with $D_1$ and U was used as the control. 40 μl of the PAP reaction and 2 μl of the PCR reaction were purified and concentrated with a Centricon® 100 microconcentrator, and the products digested by the restriction endonuclease: 2.5 U of AciI in 1X NE buffer 3; or 3 U of EaeI in 1X NE buffer 1; or 30 U of Eco0109I in NE buffer 4 with BSA (all of the above enzymes and buffers from New England Biolabs). 10 μl of the reaction was incubated at 37° C. for 2 hours. The digestion reaction was electrophoresed through a standard 2% agarose gel as described above.

Results

Principle of PAP

Figure 1B:
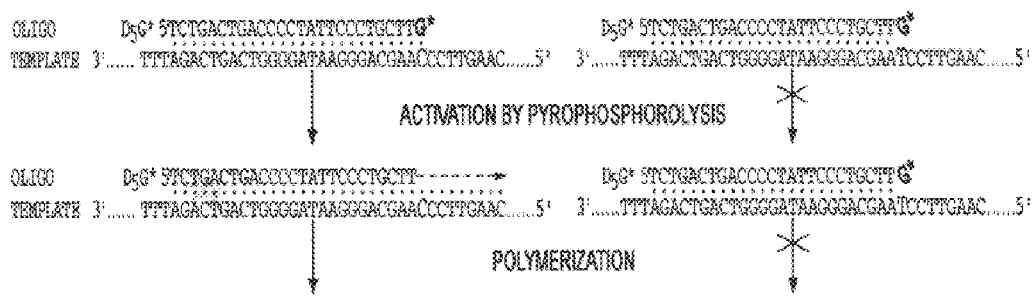
Figure 1C:
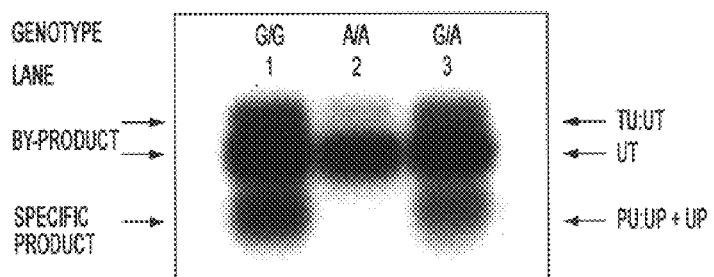
FIG. 1C is an autoradiogram of PAP from the G/G, A/A and G/A genotypes of the human dopamine receptor gene.

Tfl and Taq DNA polymerases were shown to contain pyrophosphorolysis activity (data not shown). Tfl DNA polymerase was utilized to detect the G allele at nucleotide 229 of the $D_1$ dopamine receptor gene (12) (FIG. 1A). P* was synthesized with either ddG or ddA at the 3'terminus (see Table 1). The 3' terminal dideoxynucleotide inhibits direct extension by polymerization, but can be removed by pyrophosphorolysis in the presence of pyrophosphate ($PP_i$) when the P* is specifically hybridized with the complementary strand of the G allele. The degraded oligonucleotide can be extended by polymerization in 5'-3'direction (FIGS. 1B and 1C).

The enhanced specificity of PAP relative to PASA is provided by serially coupling pyrophosphorolysis and polymerization. Significant nonspecific amplification requires mismatch pyrophosphorolysis and misincorporation by DNA polymerase, an extremely rare event (FIG. 2).

Specific Amplification with $D_5G^*$ and $D_3G^*$

Figure 3A:
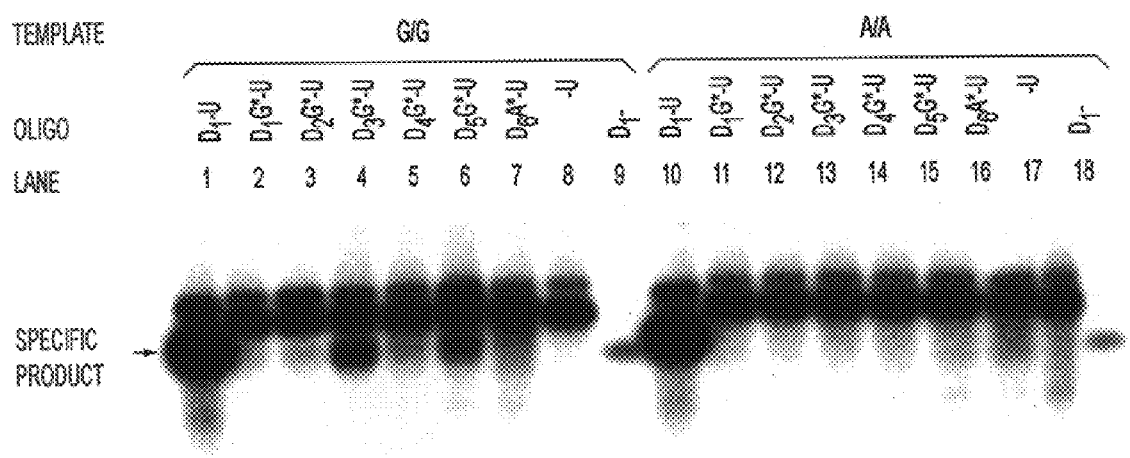
FIGS. 3A and 3B are autoradiograms showing the results of electrophoresis of samples obtained in Example 1 below.
Figure 3B:
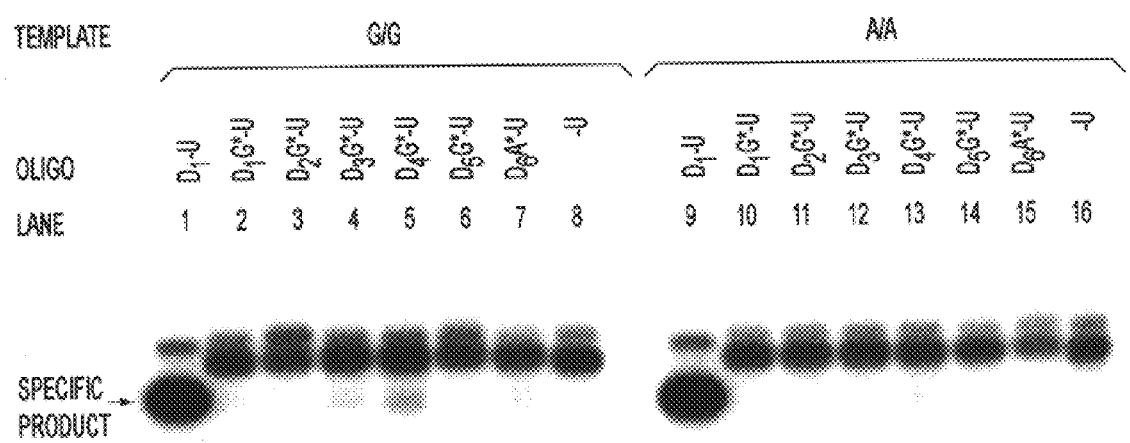

PAP was performed with two oligonucleotides (P* and U), Tfl DNA polymerase and DNA template of the G/G and A/A alleles. Multiple P* were tested (Table 1). $D_5G^*$ (the allele-specific nucleotide and dideoxynucleotide are co-localized to the 3' terminus and $D_3G^*$ (the allele-specific nucleotide is two bases from the 3' terminus) specifically amplified the G allele in the presence of $PP_i$ (FIG. 3A). Without added $PP_i$, no specific product was observed with $D_5G^*$, indicating that added $PP_i$ was an essential component for PAP (FIG. 3B, lanes 6 and 15). Faint products with $D_3G^*$ in lane 4 and with $D_4G^*$ in lane 5 were observed (FIG. 3B) (see below).

Effects of pH, [$PP_i$] and [dNTP] and Enzyme

Each of the above parameters was examined. PAP was most efficient at pH between 7.4 and 7.7, at [$PP_i$] between 200 μM and at [DNTPs] between 25 μM and 50 μM (Table 2). Taq DNA polymerase can substitute for Tfl with similar efficiencies (Table 2).

TABLE 2

Parameters affecting PAP

| Parameter | | PAP efficiency[b] | |
|---|---|---|---|
| | | $D_5G^*$-U | $D_3G^*$-U |
| pH[a] | 8.1 | – | – |
| | 7.9 | – | – |
| | 7.7 | ++ | +++ |
| | 7.5 | ++ | +++ |
| | 7.4 | ++ | +++ |
| | 7.15 | + | + |
| $PP_i^a$ | 1000 | – | – |
| (μM) | 800 | – | + |
| | 600 | – | ++ |
| | 400 | ++ | +++ |
| | 200 | ++ | +++ |
| | 0 | – | + |
| All dNTPs changed[a] | 200 | – | + |
| (μM) | 100 | – | + |
| | 50 | ++ | +++ |
| | 25 | ++ | ++++ |
| dGTP changed[a,c] | 100 | + | ++ |
| | 50 | + | ++ |
| | 25 | + | ++ |
| dATP changed[a,c] | 100 | – | + |
| | 50 | – | + |
| | 25 | – | ++ |
| Taq DNA polymerase | G allele and $PP_i$ | ++ | +++ |
| | A allele and $PP_i$ | – | – |
| | G allele and no | – | ± |

[a]Tfl DNA polymerase was used to amplify the G/G alleles under the conditions in Materials and Methods, except for the factors indicated
[b]The PAP efficiency is indicated as: –, no specific product(s); ±, very weak specific product(s); +, weak specific product(s); ++, moderate specific product(s); +++, strong specific product(s); ++++, very strong specific product(s).
[c]The indicated concentration was changed but the others were kept at 200 μM.

Identity of Specific Products

Figure 4:
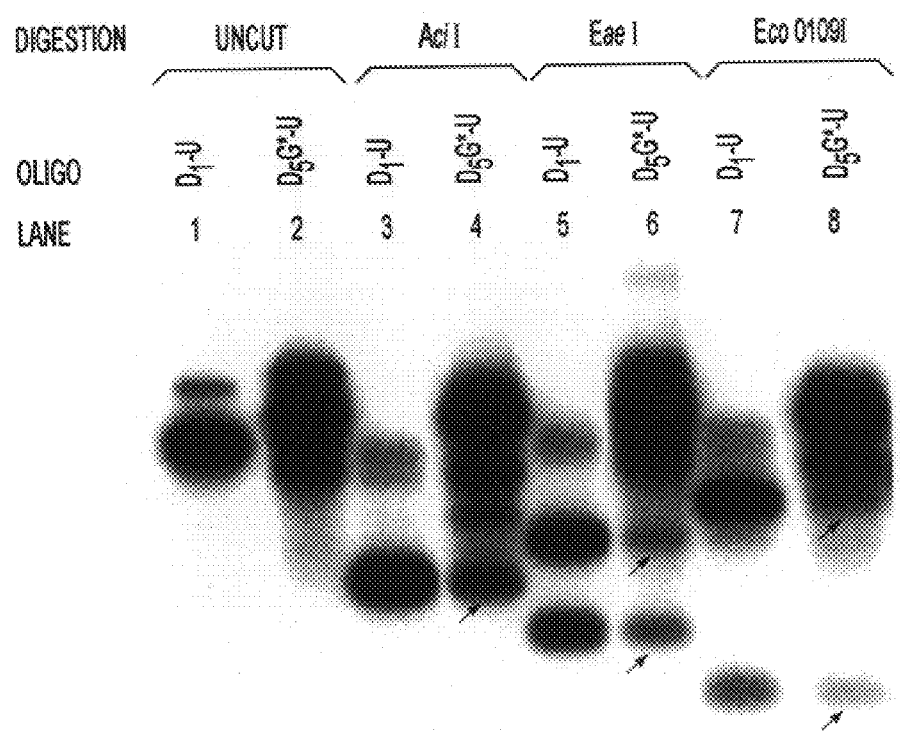
FIG. 4 is an autoradiogram showing the results of electrophoresis of samples obtained in Example 1 below.

In order to confirm the identity of the specific products, restriction endonuclease digestion was performed (FIG. 4). Each of the three restriction endonucleases of AciI, EaeI and Eco0109 has a restriction site with the PU:UP duplex. The expected restriction fragments were found. Similar results were observed with $D_3G^*$ and U.

The specific products of PAP with $D_5G^*$ and U revealed two specific bands on the agarose gel, i.e., PU:UP and UP; because U was more efficient than $D_5G^*$, under our amplification conditions. In order to confirm this, the G/G alleles were amplified by PAP using Tfl DNA polymerase with $D_5G^*$ and U as previously. The products were denatured and electrophoresed through a denaturing polyacrylamide gel. Only one specific band in single-stranded form was observed, indicating that the specific PAP products contain the duplexed and single stranded segments. The same result was observed with $D_3G^*$ and U.

Linear PAP

Figure 5:
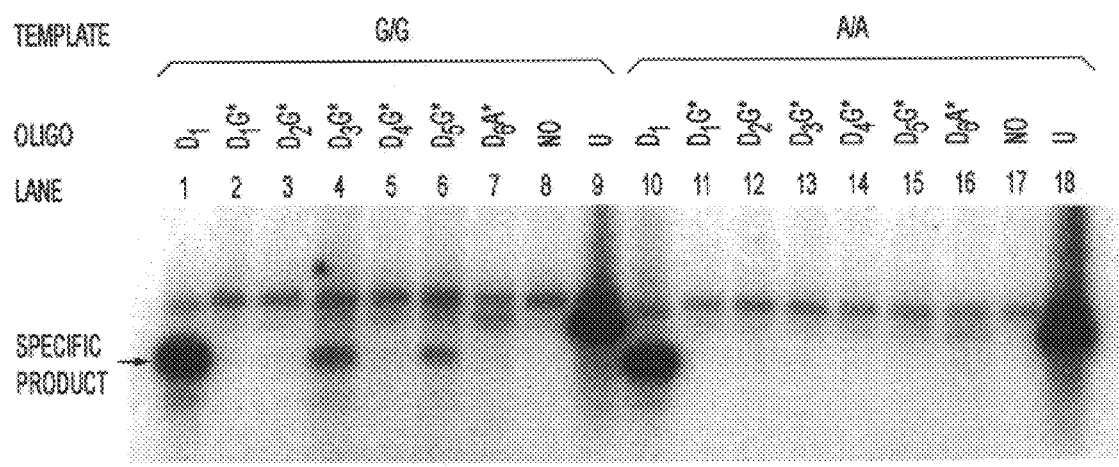
FIG. 5 is an autoradiogram showing the results of electrophoresis of samples obtained in Example 1 below.

PAP was performed for linear amplification with only one $P^*$ from the G/G and A/A alleles in the presence of $PP_i$. The specific products of PAP were obtained with $D_3G^*$ and with $D_5G^*$, but not with the other $P^*$ (FIG. 5, lanes 4 and 6). The efficiency of $P^*$ was affected by the oligonucleotide size, the 3'-terminal dideoxynucleotide and the position of the allele-specific nucleotide.

FIGS. 1A–1C. Schematic of PAP. FIG. 1A. A duplexed DNA template TU:UT is amplified with two oligonucleotides $P^*$ and U, Tfl DNA polymerase, dNTPs, pyrophosphate and [$\alpha$-$^{32}$P]-dCTP. $P^*$=pyro-phosphorolysis activatable oligonucleotide. In this example $P^*$ is $D_5G^*$ and TU:UT is a 640-bp segment of the dopamine $D_1$ receptor gene. FIG. 1B. $D_5G^*$ has a G dideoxynucleotide at the 3' terminus, and it is specific to the complementary strand of the G allele, but mismatches the A allele at the 3' terminus (Table 1). Removal of the dideoxy G by pyrophosphorolysis is followed by polymerization for each amplification. FIG. 1C. Autoradiogram of PAP from the G/G, A/A and G/A genotypes. When the G allele is present, the radioactively labeled specific products of 469 bases (duplex PU:UP and excess antisense strand UP) are produced, since the low rate of pyrophosphorolysis by Tfl polymerase implies that oligonucleotide U has a much higher efficiency than oligonucleotide $P^*$. Electrophoresis for a longer period separates PU:UP from UP. Other products of UT and UT:TU are indicated. Note that TU:UT derives from annealing of excess radioactively labeled UT with non-radioactively labeled TU original template. PAP was also performed with $D_3G^*$ and U from the G/G, A/A and G/A genotypes, and similar results were obtained.

FIGS. 2A–2B. Enhanced specificity of PAP with $D_5G^*$. The specificity of PAP is compared with that of PASA to exponentially amplify a template pool of G and A alleles. FIG. 2A. The specific amplification of PASA derives from the high efficiency of primer extension when the primer matches the G allele. The nonspecific amplification results from mismatch extension from the A allele. When this occurs, it results in an efficiency substrate for further amplification. The thickness and position of the arrow represent the amplification efficiency in each cycle. FIG. 2B. The specific amplification of PAP from the G allele occurs at high efficiency. Two types of nonspecific amplifications originate from the A allele: (i) nonspecific amplification can occur at low efficiency by mismatch pyrophosphorolysis resulting in a A:T homo-duplex PU:UP product, which is not an efficient template for subsequent amplification; (ii) nonspecific amplification can occur at extremely low efficiency by both mismatch pyrophosphorolysis and misincorporation to produce a G:T hetero-duplex PU:UP product, but once it occurs, it provides an efficiency template for subsequent amplification. A similar tendency of nonspecific amplifications is suggested for linear amplification by PAP with only $D_5G^*$. It should be noted that allele-specific nucleotide of $P^*$, such as $D_3G^*$, may be near but not at the 3' terminus. In that case nonspecific amplification of PAP requires both mismatch pyrophosphorolysis and mismatch extension. While both variations of PAP should have higher specificity than PASA, the highest specificity is predicted when the 3' terminal dideoxy nucleotide is also the allele-specific nucleotide.

FIGS. 3A–3B. Specific amplification with $D_5G^*$ and $D_3G^*$. PAP was performed in the presence (FIG. 3A) or the absence (FIG. 3B) of added $PP_i$ with two oligonucleotides for exponential amplification. The oligonucleotides are listed in Table 1. Extension controls with only U identify the positions of TU:UT and UT. Extension controls with D, identify the position of PU. PCR controls of $D_1$ and U identify the positions of PU:UP and PU:UT. Only 20% of the extension reaction with $D_1$ and the PCR reaction was loaded relative to other lanes.

FIG. 4. Restriction endonuclease digestion. To show specificity of PAP, Samples from the experiment shown in FIG. 3 were digested with AciI, EaeI and Eco0109I restriction endonucleases. Each enzyme has a restriction site within PU:UP. PAP amplified the G/G alleles with $D_5G^*$ and U, and 5% of PCR reaction with $D_1$ and U were taken as control. AciI produces a 236 bp and a 233 bp fragments from PU:UP and a 407 bp and a 233 bp fragments from TU:UT. EaeI produces a 289 bp and a 180 bp fragments from PU:UP and a 460 bp and a 180 bp fragments from TU:UT. Eco0109I produces a 348 bp and a 121 bp fragments from PU:UP and a 107 bp, a 412 bp and a 121 bp fragments from TU:UT. The arrows indicate the digestion products expected from PU:UP.

FIG. 5. Linear PAP. PAP was performed with only one $P^*$ in the presence of added $PP_i$. 20% of the reaction with $D_1$ was loaded relative to other lanes (Lanes 1 and 10). No=no oligonucleotide added.

Discussion Part I

Enhanced Specificity of PAP with $D_5G^*$

Example I provides evidence that pyrophosphorolysis followed by polymerization may be used to increase the specificity of PASA. Significant nonspecific amplification requires the serial coupling of the two types of errors (FIG. 2). The mismatch pyrophosphorolysis rate to remove a mismatch deoxynucleotide at the 3' terminus, expressed as the removal rate of an incorrect versus a correct dNMP, was reported at less than $10^{-5}$ for T7 DNA polymerase (6, 13). The misincorporation rate to create a substitution mutation by polymerization, expressed as the incorporation rate of an incorrect versus a correct dNMP, was reported as to be $10^{-5}$ for T7 DNA polymerase and to be $10^{-4}$ for E.coli DNA polymerase 1 (6, 13, 14). Similar results were reported for Taq DNA polymerase and for 3'-5' exonuclease-deficient mutants of T7 DNA polymerase and E. coli DNA polymerase I (6, 13, 15). The specificity due to the (i) nonspecific amplification in PAP with $D_5G^*$ is estimated to be $10^{-5}$ per cycle, if the mismatch pyrophosphorolysis rate of a ddNMP is the same as dNMP. The specificity due to the (ii) nonspecific amplification is estimated to be $3.3 \times 10^{-11}$, if the mismatch pyrophosphorolysis and the misincorporation are serially coupled.

Essential Components of PAP

Each $P^*$ was tested by utilizing Tfl or Taq DNA polymerases to amplify the G/G and A/A alleles. The specific amplification requires the presence of $PP_i$ and allele-specific template. In addition, the amplification efficiency is affected by the oligonucleotide size, the 3' terminal dideoxynucleotide, the position of the allele-specific nucleotide relative to the 3' terminus of $P^*$.

It is not clear why $D_1G^*$ and $D_2G^*$ did not generate the specific signals, but it may be related to a threshold stability of duplex between $P^*$ and the template. $D_6A^*$, which contains A dideoxynucleotide at the 3' terminus, did not generate the specific signal, which may be associated with different incorporation efficiencies of ddNTPs by polymerization. Klenow fragment of E. coli DNA polymerase I, Taq DNA polymerase and ΔTaq DNA polymerase incorporate ddGTP more efficiently than other ddNTPs (16, 17, 11). The rate of ddNTP incorporation also varies depending on the template sequence and can be 10-fold higher at some bases relative to others (16). Another possibility is that $D_6A^*$ is shorter in size with a lower $T_m$.

In PAP without added $PP_i$, very faint false signals were generated with $D_3G^*$ and with $D_4G^*$ (FIG. 3B). One possibility is that oligonucleotide dimers can form and trigger nonspecific pyrophosphorolysis of P* in later cycles after "endo-" $PP_i$ is released from the by-polymerization to generate UT. 3'terminal degraded $D_3G^*$ and $D_4G^*$ can be hybridized and extended as false signal. Oligonucleotide dimers were observed with $D_3G^*$ and $D_4G^*$. Another possibility with $D_3G^*$ is that the specific pyrophosphorolysis can occur in later cycles after "endo-" $PP_i$ is released. A third possibility is that $D_3G^*$ and $D_4G^*$ were contaminated by minimal $D_3$ and $D_4$ which were not fully added by G dideoxynucleotide at 3' termini.

Comparison with Other Technologies

A number of methods for enzymatic nucleic acid amplification in vitro have been developed and can be adapted to detect known sequence variants. These include polymerase chain reaction (PCR) (18, 19), ligase chain reaction (LCR) (20, 21) and rolling circle amplification (RCA) (22, 23). PAP is different in many ways: i) pyrophosphorolysis and polymerization are serially coupled for each amplification, ii) there is at least one dideoxyoligonucleotide for PAP. Other chemically modified nucleotides lacking the 3'-hydroxyl group at the 3' terminus can serve the same function, iii) one format is for linear amplification and the other is for exponential amplification, iv) $PP_i$ is necessary for the amplification, v) significant nonspecific amplification requires both mismatch pyrophosphorolysis and misincorporation, vi) PAP can detect known point mutations and greatly increase the specificity to detect an extremely rare mutant allele from the wild type allele.

The mechanistic basis is that two or more reactions are serially coupled for amplification with increased specificity. The key component of PAP is a pyrophosphorolysis activatable oligonucleotide. The blocked 3' terminus in these experiments is a dideoxy nucleotide, but any nonextendable nucleotide susceptible to pyrophosphorolysis could in principle be substituted. Indeed, any enzyme that cleaves an oligonucleotide 5' to a mismatch could serve the same function as pyrophosphorolysis activation. For example, a blocked oligonucleotide including the methylated recognition sequence (such as $G^mATC$) is annealed to its target with the unmethylated recognition sequence, then restriction endonuclease (such as DpnI) can only cleave the methylated site and so activate the oligonucleotide for extension. If a mismatch is located 5' to the cleavage site, significant nonspecific amplification requires the serial coupling of mismatch cleavage and a misincorporation, which is a rare event. Activateable oligonucleotides may also be combined with "minisequencing" primer extension. This may provide a more specific assay for detection of single base changes that might be particularly amenable to chip technology in which specificity can be a problem[24]. Demonstration that PAP can occur in the linear format (FIG. 5) supports the feasibility of this approach.

Nucleoside triphosphates and 2'-deoxynucleoside triphosphates or their chemically modified versions may be used as substrates for multiple-nucleotide extension by PAP, i.e., when one nucleotide is incorporated the extending strand can be further extended. 2',3'-dideoxynucleoside triphosphates or their chemically modified versions which are terminators for further extension may be used for single-nucleotide extension. 2',3'-dideoxynucleoside triphosphates may be labeled with radioactivity or fluorescence dye for differentiation from the 3' terminal dideoxynucleotide of oligonucleotide P*. Mixtures of nucleoside triphosphates or 2'-deoxynucleotide triphosphates and 2',3'-dideoxynucleoside triphosphates may also be used.

Discussion Part II

In PAP, specific nucleic acid sequence is produced by using the nucleic acid containing that sequence as a template. If the nucleic acid contains two strands, it is necessary to separate the strands of the nucleic acid before it can be used as the template, either as a separate step or simultaneously. The strand separation can also be accomplished by any other suitable method including physical, chemical or enzymatic means.

When it is desired to produce more than one specific product from the original nucleic acid or mixture of nucleic acids, the appropriate number of different oligonucleotides are utilized. For example, if two different specific products are to be produced exponentially, four oligonucleotides are utilized. Two of the oligonucleotides ($P^* \geq 1$) are specific for one of the specific nucleic acid sequences and the other two oligonucleotides ($P^* \geq 1$) are specific for the second specific nucleic acid sequence. In this manner, each of the two different specific sequences can be produced exponentially by the present process.

The DNA or RNA may be single- or double-stranded, may be a relatively pure species or a component of a mixture of nucleic acids, and may be linear or circular. The nucleic acid or acids may be obtained from any source, for example, from plasmid, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells by a variety of techniques such as that described by Maniatis et al. (25).

The P* oligonucleotides are selected to be "substantially" "complementary" to the different strands of each specific sequence to be amplified. Therefore, the P* oligonucleotide sequence need not reflect the exact sequence of the template. For example, a non-complementary nucleotide segment may be attached to the 5'-end of the P* oligonucleotide, with the remainder of the P* oligonucleotide sequence being complementary to the strand. Alternatively, non-complementary bases or longer sequences can be interspersed into the P* oligonucleotide, provided that the P* oligonucleotide sequence has sufficient complementarity with the sequence of the strand to be amplified to hybridize therewith and form a template for synthesis of the extension product of the other P* oligonucleotide. As used in the claims, the term "complementary" should be understood to mean "substantially complementary," as discussed herein.

Any specific nucleic acid sequence can be produced by the present process. It is only necessary that a sufficient number of bases at both ends of the sequence be known in sufficient detail so that two oligonucleotides can hybridize to different strands of the desired sequence at relative positions along the sequence. The greater the knowledge about the bases at both ends of the sequence, the greater can be the specificity of the oligonucleotides for the target nucleic acid sequence, and thus the greater the efficiency of the process. It will be understood that the word oligonucleotide as used hereinafter may refer to more than one oligonucleotide, particularly in the case where there is some ambiguity in the information regarding the terminal sequence(s) of the segment to be amplified. One oligonucleotide from this collection will be 100% homologous with the end of the desired sequence to be amplified.

The present invention can be performed in a step-wise fashion where after each step new reagents are added, or simultaneously, where all reagents are added at the initial step, or partially step-wise and partially simultaneous, where fresh reagent is added after a given number of steps. The simultaneous method may be utilized when an enzymatic means is used for the strand separation step. In the simultaneous procedure, the reaction mixture may contain the strand-separating enzyme (e.g., helicase), an appropriate energy source for the strand-separating enzyme, such as ATP. Additional materials may be added as necessary.

The nucleic acid polymerase may be any compound or system which will function to accomplish the amplification. Suitable enzymes for this purpose include, for example, Tfl DNA polymerase, Taq DNA polymerase, *E. coli* DNA polymerase I, Klenow fragment of *E. coli* DNA polymerase I, T4 DNA polymerase, T7 DNA polymerase, other available DNA polymerases, reverse transcriptase, and other genetic engineered versions. It is predicted on the basis of the relationship between reverse and forward reactions that a DNA polymerase will have high and even pyrophosphoroslysis activity for the P* activable oligonucleotide, if it incorporate ddNTPs efficiently (compared with dNTPs) and evenly (compared among the four ddNTPs). Of all the DNA polymerases, the genetic engineered version may be the best in the future, such as ThermoSequenase (2). Generally, the synthesis will be initiated at the 3' end of each oligonucleotide and proceed in the 5' direction along the template strand. However, inducing agents which initiate synthesis at the 5' end and proceed in the other direction can also be used in the PAP method as described above.

EXAMPLE 2
Preparation of Template by PCR

A 640-bp region of the human $D_1$ dopamine receptor gene was amplified by PCR with two primers (T=5' GAC CTG CAG CAA GGG AGT CAG AAG 3' (SEQ ID NO:1) and U=5' TCA TAC CGG AAA GGG CTG GAG ATA 3' (SEQ ID NO:2)). The TU:UT duplexed product spans nucleotides 33 to 672 in GenBank X55760 and the G+C content of the product is 55%. A common A to G polymorphism is located at nucleotide 229, resulting in three genotypes of G/G, A/A and G/A". The PCR volume is 50 µl: 50 mM KCl, 10 mM Tris/HCl, pH 8.3, 1.5 mM $MgCl_2$, 200 µM each of the four dNTPs, 0.1 µM of each primer, 2% DMSO, 1 U of Taq DNA polymerase (Boehringer Mannheim) and 250 ng of genomic DNA from G/G homozygote, A/A homozygote or G/A heterozygotes. Cycling conditions included: denaturation at 94° C. for 15 sec., annealing at 55° C. for 30 sec., and elongation at 72° C. for one min., for a total of 35 cycles with a GeneAmp PCR System 9600 (Perkin Elmer Applied Biosytems). The PCR product was purified from primers and other small molecules by approximately 10,000-fold by three times of retention on a Centricons 100 microconcentrator (Amicon). The amount of recovered PCR product was determined by UV absorbance at 260 nm.

Synthesis of P* by Adding a 3' dideoxynucleotide

The deoxynucleotide oligonucleotide was synthesized by Perseptive Biosystems 8909 Synthesizer (Framinsham) and purified by oligopure cartridges (Hamilton) in the City of Hope DNA/RNA Chemistry Laboratory. The 3' terminal dideoxynucleotide was added by terminal transferase. The mixture contained a total volume of 30 µl:100 mM potassium cacodylate (pH 7.2), 2.0 mM $CoCl_2$, 0.2 mM DTT, 2500 pM of the oligonucleotide, 2 mM 2',3'-ddNTP (the molar ratio of the 3'-OH terminus to ddNTP was 1:24) (Boehringer Mannheim), 100 U of terminal transferase (GIBCO BRL). The reaction was incubated at 37° C. for 4 hr and then stopped by adding EDTA at 5 mM final concentration. After desalting using a Centri-spin™ column (Princeton Separations), P* was purified by preparative 7 M urea/20% polyacrylamide gel electrophoresis in TBE buffer (90 mM Tris/borate, 1 mM EDTA, pH 8.3) (25). The amount of the recovered P* was determined by UV absorbance at 260 nm.

Since small amounts of unterminated oligonucleotide would result in nonspecificity of pyrophosphorolysis, each P* was $^{32}$P-labeled at the 5' terminus by T4 polynucleotide kinase and then was electrophoresed through a 7 M urea/20% polyacrylamide gel. Only P* products were visible even when the gel was overexposed (data not shown). It is estimated that more than 99.99% of P* contained a dideoxynucleotide at the 3' terminus. The purity of P* was supported by the absence of PCR product or PAP product at pH 8.3.

Pyrophosphorolysis Activated Polymerization

Regions from 445 to 469 bp within the TU:UT duplexed template were amplified by PAP with oligonucleotides P* and U, or with only P* . The PU:UP duplexed product corresponds to nucleotides 204–228 to 672 in GenBank X55760 and its G+C content is 56%. The PAP reaction mixture contained a total volume of 25 µl: 50 mM KCl, 10 mM Tris/HCl (pH 7.6), 1.5 mM $MgCl_2$, 100 µM each of the four dNTPs (dATP, dTTP, dGTP and dCTP), 0.1 µM P*, 0.1 µM U oligonucleotide (TCATACCGGAAAGGGCTGGAGATA (SEQ ID NO:2)), 300 µM $Na_4PP_i$, 2% DMSO, 1 µCi of [$\alpha$-$^{32}$P] dCTP (3000Ci/mmole, Amersham), 1 U of AmpliTaqFS DNA polymerase (PE Applied Biosystems) or 0.5 U of each of AmpliTaqFS and Taq DNA polymerases, and 10 ng of TU:UT. ThermoSequenase (Amersham Pharmacia) was also tested under the same conditions except for 8U ThermoSequenase or 4U ThermoSequenase plus 0.5U Taq and 2.5 mM $MgCl_2$. The cycling conditions included: denaturation at 94° C. for 10 sec., annealing at 60° C. for 1 min. (at 55° C. for ThermoSequenase), and elongation at 72° C. for 2 min., for a total of 15 cycles.

The product was electrophoresed through a standard 2% agarose gel. The gel was stained with ethidium bromide for UV photography by a CCD camera (Bio-Rad Gel Doc 1000) and Multi-Analyst® software, dried and subjected to Kodak X-OMAT™ AR film for autoradiography. The PAP yield was quantitated with a PhosphorImager with ImageQuant software (Molecular Dynamics) as the total number of pixels in the PCR band minus the background, indicated as a random unit.

Results and Discussion
Enhanced PAP Efficiency

In Example 1, only the P* with ddG at the 3' terminus was amplified using native Tfl or Taq DNA polymerase. AmpliTaqFS and ThermoSequenase DNA polymerases were found to achieve much higher PAP efficiency with much less discrimination against any kind of dideoxynucleotide (ddAMP, ddTMP, ddGMP or ddCMP) at the 3' terminus of P*. For example, P*(212)18G$^0$ and P*(212)18A$^0$, which are 18-mers of the dopamine $D_1$ receptor gene but have ddGMP and ddAMP at the 3' termini (Table 3), specifically amplified the G and A alleles, respectively. Their yield ratio was 1.4 (Compare Lanes 9 with 11 in FIG. 6B), and so P*(212)18G$^0$ is estimated to be 4% more efficient per cycle than P*(212) 18A$^0$. Another P*(228)26A= 5'TAGGAACTTGGGGGGTGTCAGAGCCC* 3' (SEQ ID NO:12), which is a 26-mer with ddCMP at the 3' terminus, was amplified as efficiently as a primer without ddCMP at the 3' terminus, and the yield was estimated to be increased 1,000 fold compared with that by using Tfl or Taq. Moreover, PAP amplified segments directly from human genomic DNA.

TABLE 3

PAP specificity affected by P* length and mismatch

| Name | Sequence (SEQ ID NO:) | Mismatch base Type | Distance[c] | $T_m$ (°C.)[d] | Noise ratio (%)[e] |
|---|---|---|---|---|---|
| P*(204)26G[0a] | 5'tctgactgACCCCTATTCCCTGCTTG*[b](13) | G | 0 | 80 | 0.0 |
| P*(208)22G[0] | 5'actgACCCCTATTCCCTGCTTG*(14) | G | 0 | 68 | 0.5 |
| P*(210)20G[0] | 5'tgACCCCTATTCCCTGCTTG*(15) | G | 0 | 62 | 0.1 |
| P*(212)18G[0] | 5'ACCCCTATTCCCTGCTTG*(16) | G | 0 | 56 | 0.3 |
| P*(216)26G[-12] | 5'ctattcccTGCTTGGGAACTTGAGGG*(17) | G | -12 | 80 | 107.1 |
| P*(220)22G[-12] | 5'tcccTGCTTGGGAACTTGAGGG*(18) | G | -12 | 70 | 95.5 |
| P*(222)20G[-12] | 5'ccTGCTTGGGAACTTGAGGG*(19) | G | -12 | 64 | 75.8 |
| P*(224)18G[-12] | 5'TGCTTGGGAACTTGAGGG*(20) | G | -12 | 56 | 7.0 |
| P*(206)26A[-2] | 5'tgactgacCCCTATTCCCTGCTTAGG*(21) | A | -2 | 80 | 30.4 |
| P*(210)22A[-2] | 5'tgacCCCTATTCCCTGCTTAGG*(22) | A | -2 | 68 | 3.3 |
| P*(212)20A[-2] | 5'acCCCTATTCCCTGCTTAGG*(23) | A | -2 | 62 | 2.0 |
| P*(214)18A[-2] | 5'CCCTATTCCCTGCTTAGG*(24) | A | -2 | 56 | 0.0 |
| P*(206)26G[-9] | 5'tgactgacCCCTATTCGCTGCTTAGG*(25) | C→G | -9 | 80 | 95.0 |
| P*(210)22G[-9] | 5'tgacCCCTATTCGCTGCTTAGG*(26) | C→G | -9 | 68 | 88.1 |
| P*(212)20G[-9] | 5'acCCCTATTCGCTGCTTAGG*(27) | C→G | -9 | 62 | 49.5 |
| P*(214)18G[-9] | 5'CCCTATTCGCTGCTTAGG*(28) | C→G | -9 | 56 | 4.7 |
| P*(206)26T[-15] | 5'tgactgacCCTTATTCCCTGCTTAGG*(29) | C→T | -15 | 78 | 89.0 |
| P*(210)22T[-15] | 5'tgacCCTTATTCCCTGCTTAGG*(30) | C→T | -15 | 66 | 47.8 |
| P*(212)20T[-15] | 5'acCCTTATTCCCTGCTTAGG*(31) | C→T | -15 | 60 | 3.4 |
| P*(214)18T[-15] | 5'CCTTATTCCCTGCTTAGG*(32) | C→T | -15 | 54 | 0.0 |

[a]P*(204)26G[0] is a P* with a G dideoxynucleotide at the 3' terminus. [0]means the allele-specific base is at the 3' terminus. The first base at 5' terminus corresponds to nucleotide 204 in GenBank X55760. Its length is 26 bases.
[b]The bold G or A are the G or A allele specific base and the underlined base is designed mismatch.
[c]The distance from the 3' terminus to the allele-specific base: 0 = at the 3' terminus, -3 = three bases from the 3' terminus.
[d]The $T_m$ for oligonucleotide was estimated to be 4° C. X(G + C) + 2° C. X(T + A) under condition of 1M NaCl. The length of each P* is 18 bases.
[e]The noise ratio of PAP (%) is defined as the relative yield of non-specific allele product to specific allele product by the same P*, or as the relative yield of the designated mutated P* to its native form by using the same template. A specific signal is denoted as <10% noise ratio.

AmpliTaqFS has two mutations compared with native Taq. One mutation in the 5' nuclease domain eliminates 5'-3' exonuclease activity and the second mutation F667Y in the active site (38). ThermoSequenase has the same mutation F667Y in the active site but a deletion of the 5'-3' exonuclease domain (39,40). They do not distinguish between dNTP and ddNTP for incorporation. The pyrophosphorolysis of ddNMPs, which is the reverse reaction, is supposed to be much higher and less discriminated by these enzymes. Although either AmpliTaqFS or ThermoSequenase DNA polymerases used was formulated to contain a thermostable pyrophosphatase (manufacturers' instructions) which can hydrolyze $PP_i$ in the reaction so as to decrease PAP efficiency, PAP was still amplified under our conditions. AmpliTaqFS and ThermoSequenase DNA polymerases will work better in their pure form without the contaminated pyrophosphatase.

The 3' Specific Subsequence of P*

Figure 7A:
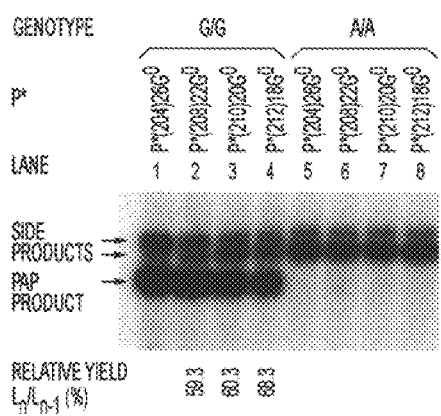

Various P*s were examined with different lengths and mismatches using AmpliTaqFS (Table 3). The effect of length and mismatch on PAP efficiency is expressed as the relative yield (%) between two P* of different lengths from the same template (FIG. 7), which varied from 0.0% to 201.5% with each two to four less bases in length The specificity of PAP is also affected by P* length and mismatch (Table 3). The noise ratio (%) is defined as the relative yield of the mismatch product to the match product, and a specific signal is scored with <10% noise ratio. If the allele-specific base of P* was at the 3' terminus, only the specific allele was amplified and the specificity was not associated with P* length (FIG. 7A). If the allele-specific base was not at the 3' terminus of P*, the specificity was associated with P* length. Any non-3'-terminal mismatch in the 18-mer P*, which was up to 15 bases from the 3' terminus, caused no amplification (FIGS. 7B to 7E), but even two such mismatches in the 26-mer P* caused non-specific amplification (data not shown).

The 18-mers were further examined using "stacked" P*s, which span the allele-specific base at different positions (Table 4). The noise ratio (%) varied from 0.0% to 7.1%. The length of the 3' specific subsequence was ≧13 bases.

TABLE 4

PAP specificity with differently positioned P*s

| Name | Sequence (SEQ ID NO:) |
|---|---|
| Template | G 5'GACTGACCCCTATTCCCTGCTT-GGAACTTGAGGGGTGTC . . . 3'(33) |

TABLE 4-continued

PAP specificity with differently positioned P*s

A
P*(212)18G⁰      5'ACCCCTATTCCCTGCTTG*(16)
P*(212)18A⁰      5'ACCCCTATTCCCTGCTTA*(34)
P*(214)18A⁻²      5'CCCTATTCCCTGCTTAGG*(24)
P*(218)18G⁻⁶      5'TTCCCTGCTTGGGAACT*(35)
P*(221)18G⁻⁹      5'CCCTGCTTGGGAACTTGA*(36)
P*(224)18G⁻¹²      5'TGCTTGGGAACTTGAGGG*(37)

| Name | 3' terminal dideoxy | Allele-specific base Type | Distance | T_m (°C.)^d | Noise ratio (%)^a Exponential PAP | Linear PAP template |
|---|---|---|---|---|---|---|
| P*(212)18G⁰ | ddG | G | 0 | 56 | 2.7 | 0.0 |
| p*(212)18A⁰ | ddA | A | 0 | 54 | 3.8 | 1.1 |
| P*(214)18A⁻² | ddG | A | -2 | 56 | 4.7 | 0.0 |
| P*(218)18G⁻⁶ | ddT | G | -6 | 54 | 0.0 | 0.0 |
| P*(221)18G⁻⁹ | ddA | G | -9 | 56 | 1.7 | 1.7 |
| P*(224)18G⁻¹² | ddG | G | -12 | 56 | 7.1 | 0.6 |

$^a$The amplification from the G and A templates by PAP with two oligonucleotides or linear PAP with one P*. The noise ratio of PAP (%) is the relative yield of the non-specific allele product to the specific allele product.

Similar results were obtained by using P*s which match and mismatch the G allele at different positions (Table 5). The noise ratio with one mismatch was various from 0.8% to 5.6%. The length of the 3' specific subsequence was ≧16 bases. The noise ratio with two mismatches was 0% (compare lane 2 with lanes 10–15 in FIG. 9).

specific subsequence ≦1) determines the specificity, i.e., within this region any mismatch to its complementary strand of the template results in no amplification; and a 5' enhancer subsequence (m=the number of bases of 5' enhancer subsequence ≧0) enhances the amplification efficiency. PAP specificity is co-determined by the base pairing specificity of

TABLE 5

PAP specificity with differently mismatched P*s

| Name | Sequence (SEQ ID NO:) | The 3' terminal dideoxy | Mismatch^a Type | Distance | T_m(°C.) | Noise ratio (%)^b Exponential PAP | Linear PAP |
|---|---|---|---|---|---|---|---|
| P*(212)18G⁰ | 5'ACCCCTATTCCCTGCTTG*(16) | ddG | | | 56 | 1.0 | 0.0 |
| P*(212)18A⁻³ | 5'ACCCCTATTCCCTGATTG*(38) | ddG | C→A | -3 | 54 | 1.3 | 0.0 |
| P*(212)18G⁻⁶ | 5'ACCCCTATTCCGTGCTTG*(39) | ddG | C→G | -6 | 56 | 0.8 | 0.6 |
| p*(212)18C⁻⁹ | 5'ACCCCTATCCCCTGCTTG*(40) | ddG | T→C | -9 | 58 | 1.8 | 0.4 |
| P*(212)18G⁻¹² | 5'ACCCCGATTCCCTGCTTG*(41) | ddG | T→G | -12 | 58 | 5.6 | 1.7 |
| P*(212)18T⁻¹⁵ | 5'ACTCCTATTCCCTGCTTG*(42) | ddG | C→T | -15 | 54 | 3.3 | 1.2 |

$^a$match or mismatch with the G allele.
$^b$noise ratio (%) is the relative yield between a mismatched P* and P*(212)18G⁰ with the G allele-specific template.

Linear PAP was examined using only 18 mer P*s and higher specificity was observed with lower noise ratio (Tables 4 and 5). Linear PAP takes a different mechanistic pathway in which every non-specific product is generated from the starting template which requires mismatched pyrophosphorolysis with the 3' terminal mismatched P*, or both mismatched pyrophosphorolysis and mismatched extension with the non-3' terminal mismatched P*.

PASA was performed with 17-mer primers without adding a ddNMP at the 3' terminus (see Tables 4 and 5). A mismatched 17-mer primer strongly amplified a nonspecific product with 30% noise ratio when the mismatch was as near as 6 bases to 3' terminus, showing a much shorter 3' specific subsequence. Similar results were reported elsewhere previously (41).

In summary, P* (1-length) has two subsequences: a 3' specific subsequence (n=the number of bases of the 3' the 3' specific subsequence, the pyrophosphorolysis specificity and the polymerization specificity. Thus, the base pairing specificity of the 3' specific subsequence is a minimum requirement of the PAP specificity.

The length of the 3' specific subsequence of P* may be affected by the sequence context and size of the P*, the type of the 3' terminal dideoxynucleotide, the template sequence, the DNA polymerase, other components like iron, and cycling conditions. When the template contains repeated sequences >1 or homogeneous polymer runs >1, P* loses specificity for anchoring.

Scanning for Unknown Sequence Variants

The property of the 3' specific subsequence of P* can be applied to scanning for unknown sequence variants or re-sequencing of predetermined sequences in a parallel way. Each nucleotide on the complementary strand of the predetermined sequence is queried by four downstream P*s, such as 18-mers (FIG. 6), which have identical sequence except that at the 3' terminus, either ddAMP, ddTMP, ddGMP or ddCMP corresponds to the wild type sequence and the three possible single base substitutions. The number of P*s scanning the complementary strand of X bases is multiplication of 4 and X, which is suitable for either exponential or linear PAP. The four downstream P*s can even be immobilized on a single dot when ddAMP, ddTMP, ddGMP and ddCMP at the 3' termini are labeled differently for differentiation, such as by four fluorescence dyes. The amplification signal can thus be represented by intensity decrease of each dye when ddNMP is removed from P* by pyrophosphorolysis. One advantage of linear PAP is that the four ddNTPs can be used as substrates for single base extensions, with are labeled with different dyes for differentiation.

Briefly, if only all the P*s corresponding the wild type sequence are specifically amplified, the wild type sequence can be arranged in order by analyzing overlaps. A P* with a single base substitution at the 3' terminus is amplified at the position of hemi- or homo-point mutations. The mutation also creates a "gap" of no PAP signal, which spans a region of several successive nucleotides. For single base substitution, the gap size (bases)+1=the length of the 3' specific subsequence.

Furthermore, we can also scan the sense strand by designing a second set of upstream P*s. An unknown single base substitution can be determined by combination of the two sets of P*s, even in heterozygotes. An unknown small deletion and insertion can be detected and localized. In order to identify a specific type of deletion or insertion, it is possible to add corresponding P*s. For fingerprinting, which can provide information of mutation position, there is a simple stacking way that the stacked region of each two successive P*s<the 3' specific subsequence on the array to reduce the number of P*s by up to n fold.

Determination of de novo DNA Sequence

The concept of de novo DNA sequencing by PAP makes use of all the possible 3' specific subsequences of P* to identify the presence of the 3' specific subsequence in de novo sequence. A complete set of the 3' specific subsequences of P* is $4^n$. Each of the 3' specific subsequence has a complete subset of the 5' enhancer subsequence of $4^m$. For example, a complete set of 16-mer as the 3' specific subsequence and 2-mer as the 5' enhancer subsequence can be indicated as (A, T, G, C)(A, T, G, C) $N_{16}=4^{18}$.

Briefly, the procedure first determines the list of all the specific PAP amplifications and then reconstructs the unknown DNA complementary sequence from this list by ordering the 3' specific subsequences with the given length by using the Watson-Crick pairing rules.

The assembly process is interrupted wherever a given 3' specific subsequence of P* is encountered two or more times. One of the factors influencing the maximum sequencing length is the length of the 3' specific subsequence. The length of a random sequence that can be reconstructed unambiguously by a complete set of the 3' specific subsequence with the given length is approximately the square root of the number of the 3' specific sequence in the complete set with ≧50% possibility that any given 3' specific subsequence is not encountered two or more times. Octamers of the 3' specific subsequence, of which there are 65,536, may be useful in the range up to 200 bases. Decanucleotides, of which there are more than a million, may analyze up to a kilobase de novo sequence. 18 mer P*s containing 16 mer as the 3' specific subsequence, which complete set is $4^{18}$ of P*s, may sequence maximum 77,332 bases.

When there is neighbored known sequence to design an opposite oligonucleotide for PAP with two oligonucleotides. The maximum sequencing length is mainly limited to the opposite oligonucleotide, but not to the length of the 3' specific subsequence of P*, termed Conditional de novo DNA sequencing.

Other Applications for PAP

For fingerprinting which compares two DNA sequences to see if they are the same or different, there is a simple way to reduce the number of P*s by using an incomplete set of the 3' specific subsequences. By arranging them in a particular order, it is possible to identify the chromosomal locations as well as sequences. Considering the $3\times10^9$ bp DNA in human genome, PAP with two oligonucleotides is preferred over PAP with only one P* to increase the specificity.

To monitor gene expression profiling, where up to $6\times10^4$ to $10^5$ transcripts are expressed and details of the precise sequence are unnecessary, PAP with only one P* can be applied and a set of P* which identify unique motifs in genes can be designed with a total length of up to 22-mer. Between each two P*s, there is at least a sequence difference at the 3' terminus or ≧2 sequence differences at the non-3' terminus.

Comparison with Sequence by Hybridization

In SBH by using oligonucleotide, the DNA sequence is determined by the hybridization and assembly of positively hybridizing probes through overlapping portions. It has been known for a long time that a single oligonucleotide hybridization on a immobilized sample can be very specific in optimal hybridization and washing conditions (42), thus it is possible to discriminate perfect hybrids from ones containing a single internal mismatch The oligonucleotides in array are 11–20 nucleotides in length and have 7–9 bases specific region in the middle, the non-specific signal is generated by mismatched hybridization. Under standard hybridization and washing conditions, the duplex stability between match and mismatch is also affected by the terminal mismatch and the flanking sequence (32, 33, 43).

SHB can be modified with enzymes in several ways (26, 44). Primer extension by DNA polymerase incorporates bases one at a time only if they match the complement strand. Ligase has similar requirements: two oligonucleotides can be joined enzymatically provided they both are complementary to the template at the position of joining.

Figure 6A:
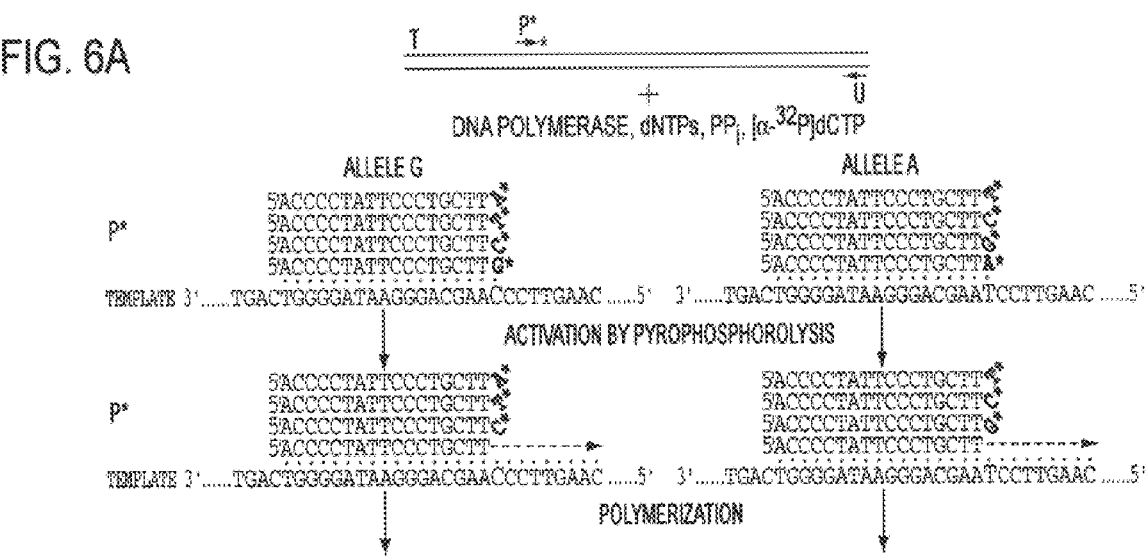
FIG. 6A is a schematic illustrating enhancement of PAP efficiency.
Figure 6B:
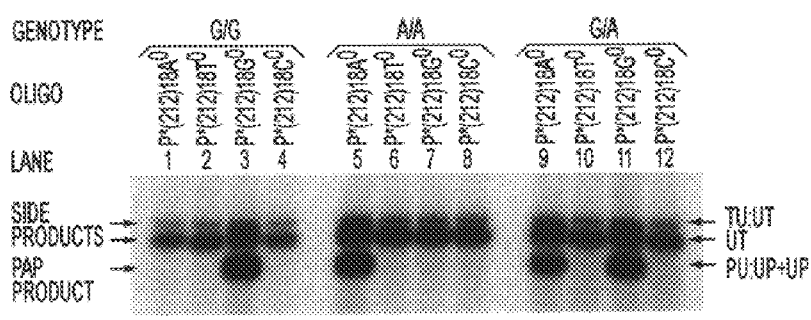
FIG. 6B is an autoradiogram of PAP from the G/G, A/A and G/A genotypes of the human dopamine receptor gene.

FIGS. 6A–6B. Enhancement of PAP efficiency. FIG. 6A. PAP is amplified with two oligonucleotides P* and U from duplex TU:UT template. Each of the four P*s has a ddA, ddT, ddG and ddC at the 3' terminus. The 3' terminal base is either specific to the complementary strand of the G or A alleles, or not matched. FIG. 6B. Autoradiogram of PAP from the G/G, A/A and G/A genotypes of the human dopamine receptor gene. The radioactively labeled specific products of 461 bases (duplex PU:UP and excess antisense strand UP) are produced. Other side products UT and UT:TU are indicated. Note that TU:UT derives from annealing of excess radioactively labeled UT with non-radioactively labeled TU original template.

Figure 7B:
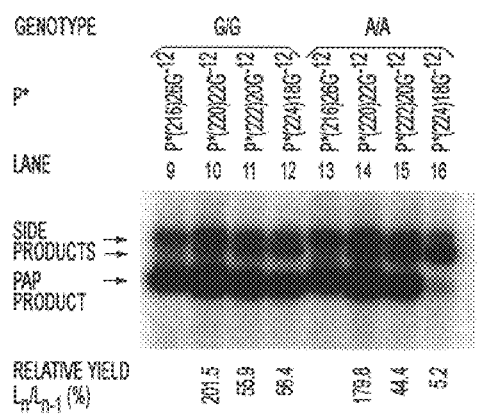

FIGS. 7A–7E. Effect of P* length and mismatch on PAP efficiency. PAP was amplified with P* and U oligonucleotide (see Table 3). In each of FIGS. 7A–7E, P*s have the sample 3' termini but are different in length. FIG. 7A. In lanes 1–4, the P*s matched and amplified the G allele. In lanes 5–8, the P*s mismatched at the 3' termini but amplified the A allele. FIG. 7B. In lanes 9–12, the P*s matched and amplified the G allele. In lanes 13–16, the P*s mismatched at −12 bases to the 3' termini but amplified the A allele. FIG. 7C. In lanes 17–20, the P*s matched and amplified the A allele. In lanes 21–24, the P*s mismatched at −2 bases to the 3' termini but amplified the G allele. FIG. 7D. In lanes 25–28, the P*s mismatched at −9 bases to the 3' termini but amplified the A allele. FIG. 7E. In lanes 29–32, the P*s mismatched at −15 bases to the 3' termini but amplified the A allele. The length effect is indicated as the yield ratio in one lane ($L_n$) to the previous lane ($L_{n-1}$). The length effect was not shown in lanes 5–8 because the signals are at or close to the background.

Figure 8:
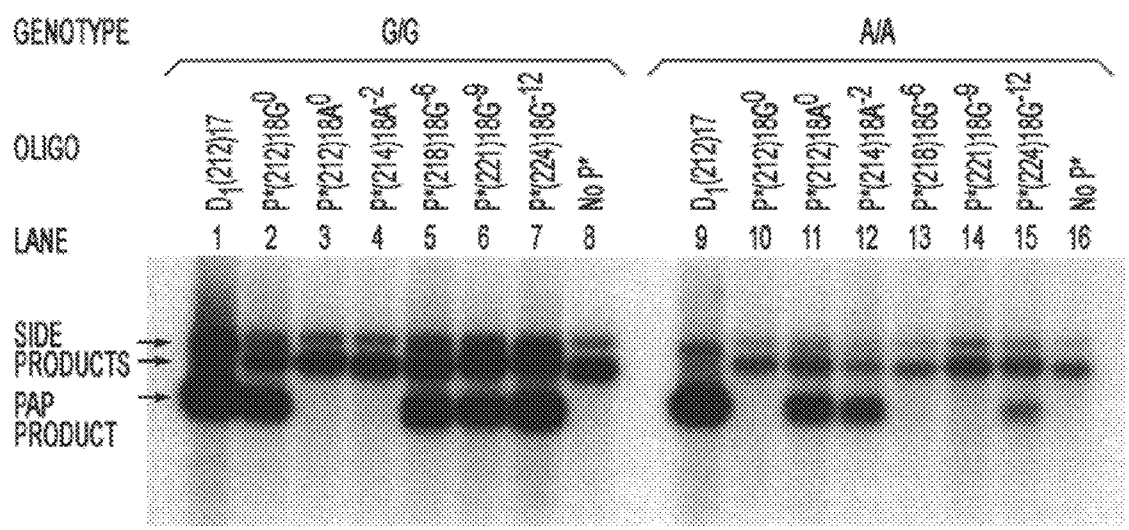
FIG. 8 is an autoradiogram showing the results of electrophoresis of samples obtained in Example 2 below.

FIG. 8. PAP specificity with differently positioned P*s. PAP was amplified with a P* and U oligonucleotide (see Table 4). The P* matched to and amplified the G allele in lanes 2–7, but mis matched to and amplified the A allele in lanes 9–15. Lanes 1 and 9 were PCR control with $D_1(212)17$ mer and U. Lanes 8 and 16 were extension control with only U.

Figure 9:
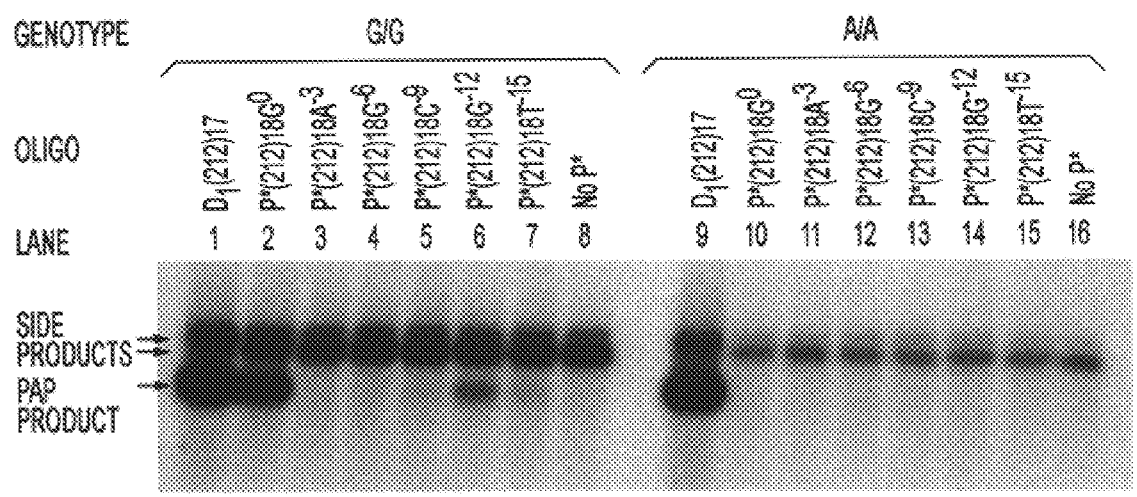
FIG. 9 is an autoradiogram showing the results of electrophoresis of samples obtained in Example 2 below.

FIG. 9. PAP specificity with differently mismatched P*s. PAP was amplified with a P* and U oligonucleotide (see Table 5). In lanes 2–7, the P* amplified the G allele with match or one mismatch. In lanes 9–15, the P* amplified the A with one or two mismatches. Lanes 1 and 9 were PCR control with $D_1(212)17$ mer and U. Lanes 8 and 16 were extension control with only U.

EXAMPLE 3

Figure 10:
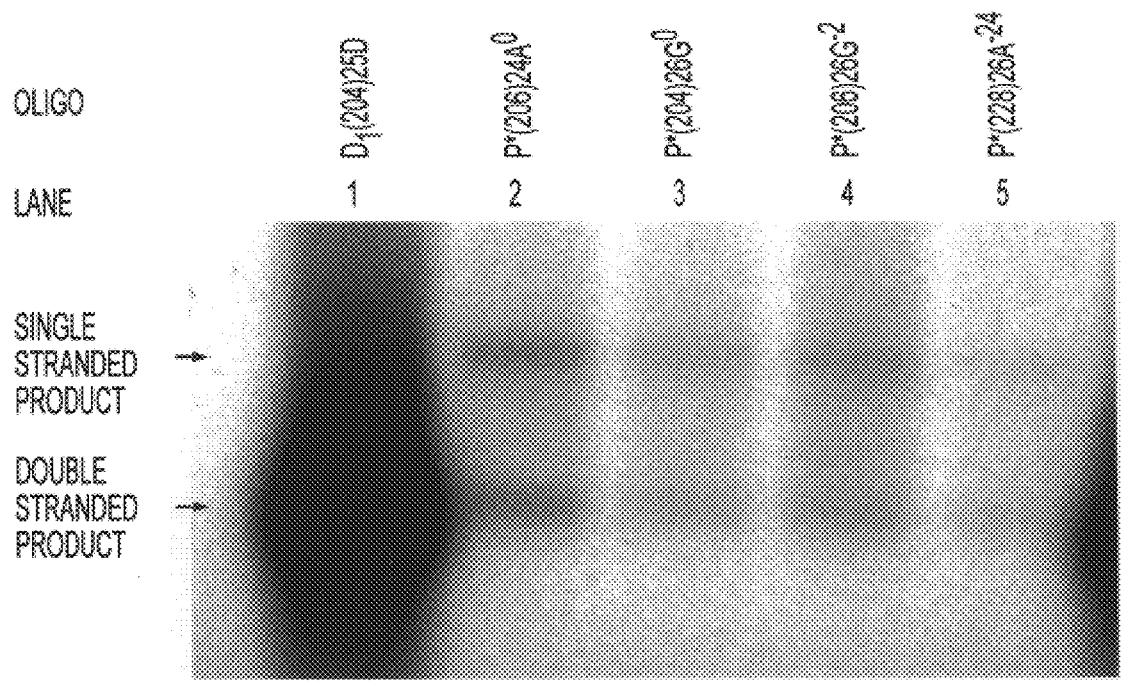
FIG. 10 is an autoradiogram showing the results of electrophoresis of samples obtained in Example 3 below.

This example illustrates PAP amplification directly from genomic DNA. The oligonucleotides used in this example are listed below. The lane numbers refer to lanes in FIG. 10.

The downstream oligonucleotides in 0.1 µM concentration are:

```
Lane:               5'TCTGACTGACCCCTATTCCCTGCTTT3'
D₁(204)25D          (SEQ ID NO:43)
Lane 2:             5'TGACTGACCCCTATTCCCTGCTTA*3'
P*(206)24A⁰         (A allele specific;
                    SEQ ID NO:44)
lane 3:             5'TCTGACTGACCCCTATTCCCTGCTTG*3'
P*(204)26G⁰         (G allele specific;
                    SEQ ID NO:45)
Lane 4:             5'ACTGACCCCTATTCCCTGCTTGGG*3'
P*(206)24G⁻²        (G allele specific;
                    SEQ ID NO:46)
Lane 5:             5'TAGGAACTTGGGGGCTGTCAGAGCCC*3'
P*(228)26A⁻²⁴       (A allele specific;
                    SEQ ID NO:47)
```

The opposite upstream oligonucleotide in 0.1 µM concentration is: $D_1(420)24U$ 5' ACGGCAGCACAGAC-CAGCGTGTTC 3' (SEQ ID NO:48), which was paired with each downstream oligonucleotide. See Footnotes of Table 3 for details.

The other components were the same as in Example 2, except for the following: 0.5 U of each of AmpliTaqFS and Taq DNA polymerases, and 100 ng of heterozygous G/A allelic genomic DNA were used per 25 µl reaction by using 30 cycles.

The PAP product size range from 193 bp to 218 bp. One double stranded and one single stranded products were observed on the gel, indicating the exhaust of $PP_i$ hydrolyzed by the contaminated thermostable pyrophosphatase.

LIST OF REFERENCES

1. Parsons, B. L. and Heflich, R. H. *Mutat. Res.* 387, 97–121 (1997).
2. Pourzand, C. and Cerutti, P. *Mutat. Res.* 288, 113–121 (1993).
3. Knoll, A., Ketting, R. P. and Sommer, S. S. *Hum. Genet.* 98, 539–545 (1996).
4. Sarkar, G., Cassady, J., Bottema, C. D. K. and Sommer, S. S. *Anal. Biochem.* 186, 64–68 (1990).
5. Duetcher, M. P. & Kornberg, A., *J. Bio. Chem.* 244, 3019–3028 (1969).
6. Kornberg, A. & Baker, T. A., *DNA Replication*, (eds Second Edition) 113–226 (W. H. Freeman and Company, New York 1992).
7. Chien, A., Edgar, D. B. & Trela, J. M., *J. Bacteriol.* 127, 1550–1557 (1976).
8. Kaledin, A. S., Sliusarenko, A. G. & Gorodetskii, S. I., Biokhimiia 46, 1576–1584 (1981).
9. Longley, M. J., Bennett, S. E. & Mosbaugh, D. W., *Nucleic Acids Res.* 18, 7317–7322 (1990).
10. Tabor, S. & Richardson, D. C. DNA sequence analysis with a modified bacteriophage T7 DNA polymerase. *J. Bio. Chem.* 265, 8322–8328 (1990).
11. Vander Horn, P. B., Davis, M. C., Cunniff, J. J., Ruan, C., McArdle, B. F., Samols, S. B., Szasz, J., Hu, G., Hujer, K. M., Domke, S. T., Brummet, S. R., Moffett, R. B., Fuller, C. W. *BioTechniques* 22, 758–762 (1997).
12. Liu, Q., Sobell, J. L. and Sommer, S. S., *Am. J Med. Genet.* (*Neuropsych. Genet.*) 60, 165–171 (1995).
13. Wong, I., Patel, S. S. & Johnson, K. A. *Biochemistry* 30, 526–537 (1991).
14. Bebenek, K., Joyce, C. M., Fitzgerald, M. P. & Kunkel, T. A. *J. Bio. Chem.* 265, 13878–13887 (1990).
15. Eckert, K. A. & Kunkel, T. A. *Nucleic Acids Res.* 18, 3739–3744 (1990).
16. Sanger, F., Nichlen S. & Coulson, A. R. *Proc. Natl. Acad. Sci. USA* 75, 5463–5467 (1977).
17. Tabor, S. & Richardson, C. C. *Proc. Natl. Acad. Sci. USA* 92, 6339–6343 (1995).
18. Saiki, R. K., Scharf, S., Faloona, F., Mullis, K. B., Horn, G. T., Erlich, H. A. & Arnheim, N. *Science* 230, 1350–1354 (1985).
19. Saiki, R. K., Gelfand, D. H., Stoffel, S., Scharf, S. J., Higuchi, R., Horn, G. T., Mullis, K. B. & Erilich, H. A. *Science* 239, 487–491 (1988).
20. Landegren, U., Kaiser, R., Sanders, J. and Hood, L. *Science* 241, 1077–1080 (1988).
21. Barany, F. *Proc. Natl. Acad. Sci. USA* 88, 189–193 (1991).
22. Lizardi, P. M., Huang, X., Zhu, Z., Bray-Ward, P., Thomas, D. C. and Ward, D. C. *Nature Genetics* 19, 225–232 (1998).
23. Banér, J., Nilsson, M., Mendel-Hartvig, M. & Landegren, U. *Nucleic Acids Res.* 26, 5073–5078 (1998).
24. Syvanen, A. C. *Hum. Mutat.* 13, 1–10 (1999).
25. Maniatis, T., Fritsch, E. F., and Sambrook, J. *Molecular Cloning: a Laboratory Manual*, Cold Spring Harbor, N.Y.: Cold Spring Harbor Laboratory, 1982.
26. Miyada, C. G. and Wallace, R. B. *Methods in Enzymology* 154, 94–107 (1987).
27. Sanger, F., Nichlen, S. & Coulson, A. R. *Proc.Natl.Acad.Sci. U.S.A.* 75, 5463–5467 (1977).
28. Maxam, A. M. & Gilbert, W. *Proc Natl Acad Sci U S A* 74, 560–564(1977).
29. Ronaghi, M., Uhlen, M. & Nyren, P. *Science* 281, 363, 365 (1998).
30. Lysov, I., Florent'ev, V. L., Khorlin, A. A., Khrapko, K. R. & Shik, V. V. *Dokl Akad Nauk SSSR* 303, 1508–1511 (1988).
31. Bains W. & Smith G. C. *JTheorBiol* 135, 303–307 (1988).
32. Drmanac, R., Labat, I., Brukner, I. & Crkvenjakov, R. *Genomics* 4, 114–128 (1989).
33. Khrapko, K. R., Lysov, Y., Khorlyn, A. A., Shick, V. V., Florentiev, V. L. & Mirzabekov, A. D. *FEBS Lett* 256. 118–122 (1989).

34. Pevzner P. A. *J Biomol Struct Dyn* 7, 63–73 (1989).
35. Southern, E. M., Maskos, U. & Elder, J. K. *Genomics* 13, 1008–1017 (1992).
36. Liu, Q., Sobell, J. L. & Sommer, S. S. *Am J.Med. Genet.(Neuropsych.Genet.)* 60, 165–171(1995).
37. Maniatis, T. Fritsch, E. F. & Sambrook, J. *Molecular cloning: a laboratory manual* (Cold Spring Harbor Laboratory, Cold Spring Harbor, N.Y., 1982).
38. Innis, M. A. & Gelfand, D. H. in *PCR APPLICATIONS Protocols for Functional Genomics* (eds Innis, M. A., Gelfand, D. H. & Sninsky, J. J.) 3–22 (Academic Press, 1999).
39. Tabor. S. & Richardson. C. C. *Proc Natl Acad Sci USA* 92, 6339–6343 (1995).
40. Van der Horn. P. B., Davis. M. C., Cunniff. J. J., et al. *BioTechniques* 22, 758–762 (1997).
41. Sarkar, G., Cassady, J., Bottema, C. D. K. & Sommer, S. S. *Anal.Biochem*. 186, 64–68 (1990).
42. Wallace, R. B., Shaffer, J., Murphy, R. F., Bonner, J., Hirose, T. & Itakura, K. *Nucleic Acids Res* 6, 3543–3557 (1979).
43. Ginot, F. *HumMutat* 10, 1–10 (1997).
44. Southern, E. M. *Trends Genet* 12, 110–115 (1996).

What is claimed is:

1. A pyrophosphorolysis activated polymerization (PAP) method of synthesizing a desired nucleic acid strand on a nucleic acid template strand which comprises serially (a) annealing to the template strand a complementary activatable oligonucleotide P* that has a non-extendable 3'-deoxynucleotide at its 3' terminus and that has no nucleotides at or near its 3' terminus that mismatch the corresponding nucleotides on the template strand, so that the terminal 3'-deoxynucleotide is hybridized to the template strand when the oligonucleotide P* is annealed, (b) pyrophosphorolyzing the resulting duplex with pyrophosphate and an enzyme that has pyrophosphorolysis activity and activates the oligonucleotide P* by removal of the hybridized terminal 3'-deoxynucleotide, and (c) polymerizing by extending the activated oligonucleotide P* on the template strand in presence of four nucleoside triphosphates and a nucleic acid polymerase to synthesize the desired nucleic acid strand.

2. The pyrophosphorolysis activated polymerization method of claim 1 that includes amplification of the desired nucleic acid strand by (d) separating the desired nucleic acid strand of step (c) from the template strand and (e) repeating steps (a)–(d) until a desired level of amplification of the desired nucleic acid strand is achieved.

3. The pyrophosphorolysis activated polymerization method of claim 2 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

4. The pyrophosphorolysis activated polymerization method claim of 2 wherein steps (a) to (c) are conducted sequentially as two or more temperature stages on a thermocycler.

5. The pyrophosphorolysis activated polymerization method of claim 4 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

6. The pyrophosphorolysis activated polymerization method of claim 2 wherein steps (a) to (c) are conducted as one temperature stage on a thermocycler.

7. The pyrophosphorolysis activated polymerization method of claim 6 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

8. The pyrophosphorolysis activated polymerization method of claim 6 wherein the DNA polymerase is also the enzyme having pyrophosphorolysis activity.

9. The pyrophosphorolysis activated polymerization method of claim 8 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

10. The pyrophosphorolysis activated polymerization method of claim 8 wherein the DNA polymerase is thermostable Tfl or Taq.

11. The pyrophosphorolysis activated polymerization method of claim 10 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

12. The pyrophosphorolysis activated polymerization method of claim 8 wherein the DNA polymerase is a genetically engineered DNA polymerase selected from the group consisting of AmpliTaqFS, ThermoSequenase and a DNA polymerase modified to contain a mutation equivalent to a F667Y mutation in TaqFS.

13. The pyrophosphorolysis activated polymerization method of claim 12 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

14. The pyrophosphorolysis activated polymerization method of claim 2 applied to allele-specific amplification, wherein the nucleic acid template strand is present in admixture with a second, allelelic nucleic acid strand that differs from the template strand so that the activatable oligonucleotide P* has at least one nucleotide at or near its 3' terminus that mismatches the corresponding nucleotide of the alleleic strand, so that in step (a) the terminal 3'-deoxynucleotide of oligonucleotide P* is not hybridized to the allelelic strand; and thus in step (b) the pyrophosphate and enzyme that has pyrophosphorolysis activity do not substantially remove the non-hybridized terminal 3'-deoxynucleotide from the activatable oligonucleotide P* and in step (c) the oligonucleotide P* is not substantially extended by polymerization on the allelic strand, whereby the desired nucleic acid strand synthesized on the template strand is amplified preferentially over any nucleic acid strand synthesized on the allelelic strand.

15. The pyrophosphorolysis activated polymerization method of claim 14 wherein the mismatch between the activatable oligonucleotide P* and the template strand occurs at the terminal 3'-deoxynucleotide or at the first or second nucleotide from the terminal 3'-deoxynucleotide.

16. The pyrophosphorolysis activated polymerization method of claim 14 wherein the mismatch between the activatable oligonucleotide P* and the template strand occurs at the terminal 3'-deoxynucleotide.

17. The pyrophosphorolysis activated polymerization method of claim 14 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

18. The pyrophosphorolysis activated polymerization method of claim 17 wherein the mismatch between the activatable oligonucleotide P* and the template strand occurs at the terminal 3'-deoxynucleotide or at the first or second nucleotide from the terminal 3'-deoxynucleotide.

19. The pyrophosphorolysis activated polymerization method of claim 17 wherein the mismatch between the activatable oligonucleotide P* and the template strand occurs at the terminal 3'-deoxynucleotide.

20. The pyrophosphorolysis activated polymerization method of claim 17, wherein the desired nucleic acid strand, the template strand, and the alleleic strand are DNA strands, the activatable oligonucleotide P* and the second oligonucleotide are both 2'-deoxyoligonucleotides, the terminal deoxynucleotide is a 2',3'-dideoxynucleotide, the four nucleoside triphosphates are 2'-deoxynucleoside triphosphates, and the nucleic acid polymerase is a DNA polymerase.

21. The pyrophosphorolysis activated polymerization method of claim 20 wherein the mismatch between the activatable 2'-deoxyoligonucleotide P* and the template strand occurs at the terminal 2',3'-deoxynucleotide or at the first or second 2'-deoxynucleotide from the terminal 2',3'-deoxynucleotide.

22. The pyrophosphorolysis activated polymerization method of claim 20 wherein the mismatch between the activatable 2'-deoxyoligonucleotide P* and the template strand occurs at the terminal 2',3'-deoxynucleotide.

23. The pyrophosphorolysis activated polymerization method of claim 14, wherein the desired nucleic acid strand, the template strand, and the alleleic strand are DNA strands, the activatable oligonucleotide P* is a 2'-deoxyoligonucleotide, the terminal deoxynucleotide is a 2',3'-dideoxynucleotide, the four nucleoside triphosphates are 2'-deoxynucleoside triphosphates, and the nucleic acid polymerase is a DNA polymerase.

24. The pyrophosphorolysis activated polymerization method of claim 23 wherein the mismatch between the activatable oligonucleotide P* and the template strand occurs at the terminal 3'-deoxynucleotide or at the first or second nucleotide from the terminal 3'-deoxynucleotide.

25. The pyrophosphorolysis activated polymerization method of claim 23 wherein the mismatch between the activatable oligonucleotide P* and the template strand-occurs at the terminal 3'-deoxynucleotide.

26. The pyrophosphorolysis activated polymerization method of claim 23 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

27. The pyrophosphorolysis activated polymerization method of claim 26 wherein the mismatch between the activatable oligonucleotide P* and the template strand occurs at the terminal 3'-deoxynucleotide or at the first or second nucleotide from the terminal 3'-deoxynucleotide.

28. The pyrophosphorolysis activated polymerization method of claim 26 wherein the mismatch between the activatable oligonucleotide P* and the template strand occurs at the terminal 3'-deoxynucleotide.

29. The method of claim 1 wherein the nucleic acid polymerase used in step (c) is a genetically modified DNA polymerase selected from the group consisting of AmpliTaqFS, ThermoSequenase and DNA polymerase modified to contain a mutation in its active site equivalent to a F667Y mutation in TaqFS.

30. The method of claim 29 wherein PAP efficiency is enhanced or PAP efficiency is less discriminated against any kind of dideoxynucleotide at the 3' terminus of P*.

31. The method of claim 29 wherein the non-extendable 3'-deoxynucleotide at the 3' terminus of P* is a dideoxynucleotide.

32. The method of claim 31 wherein the dideoxynucleotide is labeled by dyes.

33. The method of claim 29 wherein the nucleoside triphosphates are dideoxynucleotide triphosphates as substrates of DNA polymerase.

34. The method of claim 33 wherein the dideoxynucleotide triphosphates are labeled by dyes.

35. The method of claim 1 wherein P* has a 3' specific subsequence with length n >3 nucleotides, and P* is not substantially amplified when one or more mismatches to its template strand is located within the 3' specific subsequence, while P* is substantially amplified with its perfectly matched template strand within the 3' specific subsequence.

36. The method of claim 35 wherein the mismatch in the 3' specific subsequence is within 16 nucleotides of the 3' terminus of P*.

37. The method of claim 35 wherein PAP is applied with one P* or two oligonucleotides.

38. The method of claim 1 to compare two DNA sequences or to monitor gene expression profiling, wherein a set of P*s with different 3' specific subsequences are applied for PAP.

39. The method of claim 38 wherein each P* has a 3' specific subsequence.

40. The method of claim 38 wherein the set of P* is incomplete with different 3' specific subsequences.

41. The method of claim 38 wherein a list of the specific PAP amplifications with the set of P*s are scored and then a DNA sequence complementary to the template strand of the nucleic acid is determined by ordering the 3' specific subsequences.

42. The method of claim 41 wherein PAP is applied with one P* or two oligonucleotides.

43. A pyrophosphorolysis activated polymerization method for exponential amplification of a mutant allele that is present in admixture with a wild-type allele, which comprises preparing single-stranded DNA for each allele, one single stranded DNA for each allele being a template strand and the other being a complementary strand and then serially (a) annealing to the template strand of each allele a complementary activatable 2'-deoxyoligonucleotide P* that has a non-extendable 2',3'-deoxynucleotide at its 3' terminus and that has no 2'-deoxynucleotides at or near its 3' terminus that mismatch the corresponding 2'-deoxynucleotides on the template strand of the mutant allele but that has at least one 2'-deoxynucleotide at or near its 3' terminus that mismatches the corresponding 2'-deoxynucleotide on the template stand of the wild-type allele, so that the terminal 2',3'-deoxynucleotide is hybridized to the mutant template strand but not to the wild-type template strand when the oligonucleotide P* is annealed, and simultaneously annealing to the complementary strand of each allele a second, complementary 2'-deoxyoligonucleotide, where the activatable 2'-deoxyoligonucleotide P* and the second 2'-deoxyoligonucleotide flank the region of the gene to be amplified;

(b) pyrophosphorolyzing the activatable 2'-deoxyoligonucleotide P* that is annealed to a mutant template strand with pyrophosphate and an enzyme that has pyrophosphorolysis activity to activate the 2'-deoxyoligonucleotide P* by removal of the hybridized terminal 2',3'-deoxynucleotide, and (c) polymerizing by extending the activated oligonucleotide P* on the mutant template strand in presence of four nucleoside triphosphates and a DNA polymerase and simultaneously extending the second 2'-deoxyoligonucleotide on both mutant and wild-type complementary strands, (d) separating the extension products of step (c); and (e) repeating steps (a)–(d) until the desired level of exponential amplification of the mutant allele has been achieved.

44. The pyrophosphorolysis activated polymerization method of claim 43 wherein the mismatch between the activatable 2'-deoxyoligonucleotide P* and the wild-type template strand occurs at the terminal 2',3'-deoxynucleotide or at the first or second 2'-deoxynucleotide from the terminal 2',3'-deoxynucleotide.

45. The pyrophosphorolysis activated polymerization method of claim 44 wherein the mismatch between the activatable 2'-deoxyoligonucleotide P* and the wild-type template strand occurs at the terminal 2',3'-deoxynucleotide.

46. The pyrophosphorolysis activated polymerization method of claim 43 wherein the activatable 2'-deoxyoligonucleotide P* is annealed to the complementary strands of the alleles and the second 2'-deoxyoligonucleotide is annealed to the template strands.

47. The pyrophosphorolysis activated polymerization method of claim 46 wherein the mismatch between the activatable 2'-deoxyoligonucleotide P* and the wild-type template strand occurs at the terminal 2',3'-deoxynucleotide or at the first or second 2'-deoxynucleotide from the terminal 2',3'-deoxynucleotide.

48. The pyrophosphorolysis activated polymerization method of claim 46 wherein the mismatch between the activatable 2'-deoxyoligonucleotide P* and the wild-type template strand occurs at the terminal 2',3'-deoxynucleotide.

49. The pyrophosphorolysis activated polymerization method claim of 43 wherein steps (a) to (c) are conducted sequentially as two or more temperature stages on a thermocycler.

50. The pyrophosphorolysis activated polymerization method of claim 43 wherein steps (a) to (c) are conducted as one temperature stage on a thermocycler.

51. The pyrophosphorolysis activated polymerization method of claim 43 wherein the DNA polymerase is thermostable Tfl or Taq.

52. The pyrophosphorolysis activated polymerization method of claim 43 wherein the DNA polymerase is a genetically engineered DNA polymerase selected from the group consisting of AmpliTaqFS, ThermoSequenase and a DNA polymerase modified to contain a mutation equivalent to a F667Y mutation in TaqFS.

53. A pyrophosphorolysis activated polymerization method which comprises serially
(a) annealing to a template nucleic acid strand a complementary activatable oligonucleotide P* that has a non-extendable 3'-deoxynucleotide at its 3' terminus and that has no nucleotides at or near its 3' terminus that mismatch the corresponding nucleotides on the template strand, so that the terminal 3'-deoxynucleotide is hybridized to the template strand when the oligonucleotide P* is annealed,
(b) pyrophosphorolyzing the resulting duplex with pyrophosphate and an enzyme that has pyrophosphorolysis activity and activates the oligonucleotide P* by removal of the hybridized terminal 3'-deoxynucleotide, and
(c) extending the activated oligonucleotide P* on the template strand in presence of a non-extendable 3'-deoxynucleoside triphosphate and a nucleic acid polymerase.

54. The pyrophosphorolysis activated polymerization method of claim 53 wherein the non-extendable 3'-deoxynucloside triphosphate is labeled with a radioactive or fluorescent label.

55. The pyrophosphorolysis activated polymerization method of claim 53 wherein the non-extendable 3'-deoxynucleoside triphosphate is a non-extendable 2',3'-dideoxynucleoside triphosphate.

56. The pyrophosphorolysis activated polymerization method of claim 55 wherein, in step (c), the activated oligonucleotide P* is extended in presence of a mixture of a non-extendable 2',3'-dideoxynucleoside triphosphate and four 2'-deoxy- nucleoside triphosphates.

57. The pyrophosphorolysis activated polymerization method of claim 56 wherein the non-extendable 3'-deoxynucleoside triphosphate is labeled with a radioactive or fluorescent label.

58. The pyrophosphorolysis activated polymerization method of claim 55 wherein the non-extendable 3'-deoxynucleoside triphosphate is labeled with a radioactive or fluorescent label.

59. The pyrophosphorolysis activated polymerization method of claim 53 wherein, in step (c), the activated oligonucleotide P* is extended in presence of a mixture of a non-extendable 3'-deoxynucleoside triphosphate and four nucleoside triphosphates.

60. The pyrophosphorolysis activated polymerization method of claim 59 wherein the non-extendable 3'-deoxynucleoside triphosphate is labeled with a radioactive or fluorescent label.

61. A method of scanning for unknown sequence variants in a nucleic acid sequence or re-sequencing of a predetermined sequence in a nucleic acid by pyrophosphorolysis activated polymerization (PAP) which comprises
(a) mixing under hybridization conditions a template strand of the nucleic acid with multiple sets of four activatable oligonucleotides P* which are sufficiently complementary to the template strand to hybridize therewith and which, within each set differ, from each other in having a different 3'-terminal non-extendable nucleotide, so that the 3' terminal non-extendable nucleotide is hybridized to the template strand if the template strand is complementary to the 3' terminal non-extendable nucleotide, the number of sets corresponding to the number of nucleotides in the sequence;
(b) treating the resulting duplexes with pyrophosphate and an enzyme that has pyrophosphorolysis activity to activate by pyrophosphorolysis only those oligonucleotides P* which have a 3' terminal non-extendable nucleotide that is hybridized to the template strand,
(c) polymerizing by extending the activated oligonucleotides P* on the template strand in presence of four nucleoside triphosphates and a nucleic acid polymerase,
(d) separating the nucleic acid strands synthesized in step (c) from the template strand,
(e) repeating steps (a)–(d) until a desired level of amplification is achieved, and
(f) arranging the nucleic acid sequence in order by analyzing overlaps of oligonuclotides P* that produced amplifications.

62. The method of claim 61 wherein the nucleoside triphosphates are didexonucleotide triphosphates as substrates of DNA polymerase for single nucleotide extensions.

63. The method of claim 62 wherein the dideoxynucleotide triphosphates are labeled by dyes.

64. The method of claim 61 wherein there is one P* whose 3' terminal nucleotide corresponds to a wild-type base or one of three possible single base substitutions.

65. The method of claim 61 wherein there are four P*s which have identical sequence except that at the 3' terminus, either ddAMP, ddTMP, ddGMP or ddCMP corresponds to a wild-type base and three possible single base substitutions.

66. The method of claim 65 wherein the four P*s are immobilized on a single spot.

67. The method of claim 65 wherein a list of the specific PAP amplifications with the sets of P* are scored and then a DNA sequence complementary to the template strand of the nucleic acid is reconstructed by using Watson-Crick pairing rules.

68. The method of claim 65 wherein PAP is applied with one P* or two oligonucleotides.

69. A method of determining de novo the sequence of a nucleic acid by pyrophosphorolysis activated polymerization (PAP) which comprises
(a) mixing under hybridization conditions a template strand of the nucleic acid with multiple activatable oligonucleotides P*, all having the same number n of nucleotides and constituting collectively all possible sequences having n nucleotides, and all having a non-extendable nucleotide at the 3' terminus, whereby any oligonucleotides P* that are sufficiently complementary will hybridize to the template strand, and the 3' terminal non-extendable nucleotide will hybridize to the template strand only if the template strand is complementary at the position corresponding to the 3' terminus;
(b) treating the resulting duplexes with pyrophosphate and an enzyme that has pyrophosphorolysis activity to activate only those hybridized oligonucleotides P* which have a 3' terminal non-extendable nucleotide that is hybridized to the template strand, by pyrophosphorolysis of those hybridized 3' terminal non-extendable nucleotides;
(c) polymerizing by extending the activated oligonucleotides P* on the template strand in presence of four nucleoside triphosphates and a nucleic acid polymerase,
(d) separating the nucleic acid strands synthesized in step (c) from the template strand,
(e) repeating steps (a)–(d) until a desired level of amplification has been achieved, and
(f) determining the sequence of oligonucleotides P* that produced amplifications, then arranging the nucleic acid sequence in order by analyzing overlaps of these oligonucleotides.

70. The method of claim 69 wherein the nucleoside triphosphates are didexonucleotide triphosphates as substrates of DNA polymerase for single nucleotide extensions.

71. The method of claim 70 wherein the dideoxynucleotide triphosphates are labeled by dyes.

72. The method of claim 69 wherein the dideoxynucleotide at the 3' terminus of P* is labeled by dyes.

73. The method of claim 69 wherein a set of P*s with different 3' specific subsequences are applied for PAP.

74. The method of claim 73 wherein each two successive P*s are stacked arranged with the stacked region ≦ the 3' specific subsequence to reduce the number of P*s required.

75. The method of claim 73 wherein each P* has a 3' specific subsequence.

76. The method of claim 73 wherein the set of P*s is a complete set of different 3' specific subsequences or an incomplete set of different 3' specific subsequences.

77. The method of claim 73 wherein a list of the specific PAP amplifications with the set of P*s are scored and then a DNA sequence complementary to the template strand of the nucleic acid is reconstructed by ordering the 3' specific subsequences by using Watson-Crick pairing rules.

78. The method of claim 73 wherein PAP is applied with one or two P* or two oligonucleotides.

79. A pyrophosphorolysis activated polymerization method of synthesizing a desired nucleic acid strand on a nucleic acid template strand which comprises serially
(a) annealing to the template strand a complementary activatable oligonucleotide P* that has a non-extendable 3'-deoxynucleotide at its 3' terminus and has a mismatch at its 3' terminus or at the first or second nucleotide from its 3' terminus with respect to the corresponding nucleotide on the template strand,
(b) pyrophosphorolyzing the resulting duplex with pyrophosphate and an enzyme that has pyrophosphorolysis activity and activates the oligonucleotide P* by removal of the hybridized terminal 3'-deoxynucleotide, and
(c) polymerizing by extending the activated oligonucleotide P* on the template strand in presence of four nucleoside triphosphates and a nucleic acid polymerase to synthesize the desired nucleic acid strand.

80. The pyrophosphorolysis activated polymerization method of claim 79 that includes amplification of the desired nucleic acid strand by
(d) separating the desired nucleic acid strand of step (c) from the template strand and
(e) repeating steps (a)–(d) until a desired level of amplification of the desired nucleic acid strand is achieved.

81. The pyrophosphorolysis activated polymerization method of claim 80 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

82. The pyrophosphorolysis activated polymerization method of claim 81 wherein the mismatch between the activatable oligonucleotide P* and the template strand occurs at the terminal 3'-deoxynucleotide.

83. The pyrophosphorolysis activated polymerization method claim of 80 wherein steps (a) to (c) are conducted sequentially as two or more temperature stages on a thermocycler.

84. The pyrophosphorolysis activated polymerization method of claim 83 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

85. The pyrophosphorolysis activated polymerization method of claim 84 wherein the mismatch between the activatable oligonucleotide P* and the template strand occurs at the terminal 3'-deoxynucleotide.

86. The pyrophosphorolysis activated polymerization method of claim 80 wherein steps (a) to (c) are conducted as one temperature stage on a thermocycler.

87. The pyrophosphorolysis activated polymerization method of claim 86 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

88. The pyrophosphorolysis activated polymerization method of claim 87 wherein the mismatch between the activatable oligonucleotide P* and the template strand occurs at the terminal 3'-deoxynucleotide.

89. The pyrophosphorolysis activated polymerization method of claim 86 wherein the DNA polymerase is also the enzyme having pyrophosphorolysis activity.

90. The pyrophosphorolysis activated polymerization method of claim 89 wherein the mismatch between the activatable oligonucleotide P* and the template strand occurs at the terminal 3'-deoxynucleotide.

91. The pyrophosphorolysis activated polymerization method of claim 89 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

92. The pyrophosphorolysis activated polymerization method of claim 91 wherein the mismatch between the activatable oligonucleotide P* and the template strand occurs at the terminal 3'-deoxynucleotide.

93. The pyrophosphorolysis activated polymerization method of claim 89 wherein the DNA polymerase is thermostable Tfl or Taq.

94. The pyrophosphorolysis activated polymerization method of claim 93 wherein the mismatch between the activatable oligonucleotide P* and the template strand occurs at the terminal 3'-deoxynucleotide.

95. The pyrophosphorolysis activated polymerization method of claim 93 carried out in the presence of a second oligonucleotide that in step (a) anneals to the separated desired nucleic acid strand product of step (d), and wherein step (c) includes polymerizing by extending the second oligonucleotide on the desired nucleic acid strand to synthesize a copy of the nucleic acid template strand, and step (d) includes separating the synthesized nucleic acid template strand from the desired nucleic acid strand, so that amplification is exponential.

96. The pyrophosphorolysis activated polymerization method of claim 95 wherein the mismatch between the activatable oligonucleotide P* and the template strand occurs at the terminal 3'-deoxynucleotide.

97. The pyrophosphorolysis activated polymerization method of claim 89 wherein the DNA polymerase is a genetically engineered DNA polymerase selected from the group consisting of AmpliTaqFS, ThermoSequenase and a DNA polymerase modified to contain a mutation equivalent to a F667Y mutation in TaqFS.

98. The pyrophosphorolysis activated polymerization method of claim 97 wherein the mismatch between the activatable oligonucleotide P* and the template strand occurs at the terminal 3'-deoxynucleotide.

* * * * *

UNITED STATES PATENT AND TRADEMARK OFFICE
CERTIFICATE OF CORRECTION

PATENT NO.    : 6,534,269 B2
DATED         : March 18, 2003
INVENTOR(S)   : Liu et al.

It is certified that error appears in the above-identified patent and that said Letters Patent is hereby corrected as shown below:

Column 10,
Line 16, insert after "200$\mu$M" -- and 400$\mu$M --

Column 12,
Line 4, "D" should read as -- $D_1$ --

Signed and Sealed this

Eighth Day of June, 2004

JON W. DUDAS
*Acting Director of the United States Patent and Trademark Office*

SEQUENCE LISTING

<160> NUMBER OF SEQ ID NOS: 47

<210> SEQ ID NO 1
<211> LENGTH: 24
<212> TYPE: DNA
<213> ORGANISM: Artificial Sequence
<220> FEATURE:
<223> OTHER INFORMATION: amplification primer

<400> SEQUENCE: 1
gacctgcagc aagggagtca gaag                                    24

<210> SEQ ID NO 2
<211> LENGTH: 24
<212> TYPE: DNA
<213> ORGANISM: Artificial Sequence
<220> FEATURE:
<223> OTHER INFORMATION: amplification primer

<400> SEQUENCE: 2
tcataccgga aagggctgga gata                                    24

<210> SEQ ID NO 3
<211> LENGTH: 33
<212> TYPE: DNA
<213> ORGANISM: Homo sapiens

<400> SEQUENCE: 3
aatctgactg acccctattc cctgcttrgg aac                          33

<210> SEQ ID NO 4
<211> LENGTH: 21
<212> TYPE: DNA
<213> ORGANISM: Artificial Sequence
<220> FEATURE:
<223> OTHER INFORMATION: oligonucleotide

<400> SEQUENCE: 4
actgacccct attccctgct t                                       21

<210> SEQ ID NO 5
<211> LENGTH: 22
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (22)..(22)
<223> OTHER INFORMATION: dideoxynucleotide

<400> SEQUENCE: 5
actgacccct attccctgct tg                                              22

<210> SEQ ID NO 6
<211> LENGTH: 23
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (23)..(23)
<223> OTHER INFORMATION: dideoxynucleotide

<400> SEQUENCE: 6
actgacccct attccctgct tgg                                             23

<210> SEQ ID NO 7
<211> LENGTH: 24
<212> TYPE: DNA
<213> ORGANISM: Artificial Sequence
<220> FEATURE:
<223> OTHER INFORMATION: oligoculeotide
<221> NAME/KEY: misc_feature
<222> LOCATION: (24)..(24)
<223> OTHER INFORMATION: dideoxynucleotide

<400> SEQUENCE: 7
actgacccct attccctgct tggg                                            24

<210> SEQ ID NO 8
<211> LENGTH: 25
<212> TYPE: DNA
<213> ORGANISM: Artificial Sequence
<220> FEATURE:
<223> OTHER INFORMATION: oligoculeotide
<221> NAME/KEY: misc_feature
<222> LOCATION: (25)..(25)
<223> OTHER INFORMATION: dideoxynucleotide

<400> SEQUENCE: 8
actgacccct attccctgct tgggg                                           25

<210> SEQ ID NO 9
<211> LENGTH: 26
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (26)..(26)
<223> OTHER INFORMATION: dideoxynucleotide

<400> SEQUENCE: 9
tctgactgac ccctattccc tgcttg                                          26

<210> SEQ ID NO 10
<211> LENGTH: 24
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (24)..(24)
<223> OTHER INFORMATION: dideoxynucleotide

<400> SEQUENCE: 10
tgactgaccc ctattccctg ctta                                            24

<210> SEQ ID NO 11

```
<211> LENGTH: 24
<212> TYPE: DNA
<213> ORGANISM: Artificial Sequence
<220> FEATURE:
<223> OTHER INFORMATION: oligoculeotide

<400> SEQUENCE: 11
tcataccgga aagggctgga gata                                        24

<210> SEQ ID NO 12
<211> LENGTH: 26
<212> TYPE: DNA
<213> ORGANISM: Artificial Sequence
<220> FEATURE:
<223> OTHER INFORMATION: oligonucleotide

<400> SEQUENCE: 12
taggaacttg gggggtgtca gagccc                                      26

<210> SEQ ID NO 13
<211> LENGTH: 26
<212> TYPE: DNA
<213> ORGANISM: Artificial Sequence
<220> FEATURE:
<223> OTHER INFORMATION: oligonucleotide

<400> SEQUENCE: 13
tctgactgac ccctattccc tgcttg                                      26

<210> SEQ ID NO 14
<211> LENGTH: 22
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (22)..(22)
<223> OTHER INFORMATION: dideoxynucleotide

<400> SEQUENCE: 14
actgacccct attccctgct tg                                          22

<210> SEQ ID NO 15
<211> LENGTH: 20
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (20)..(20)
<223> OTHER INFORMATION: dideoxynucleotide

<400> SEQUENCE: 15 tgaccccctat tccctgcttg                                            20

<210> SEQ ID NO 16
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 16 accccctattc cctgcttg                                              18
```

```
<210> SEQ ID NO 17
<211> LENGTH: 26
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (26)..(26)
<223> OTHER INFORMATION: dideoxynucleotide

<400> SEQUENCE: 17
ctattccctg cttgggaact tgaggg                                26

<210> SEQ ID NO 18
<211> LENGTH: 22
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (22)..(22)
<223> OTHER INFORMATION: dideoxynucleotide

<400> SEQUENCE: 18
tccctgcttg ggaacttgag gg                                    22

<210> SEQ ID NO 19
<211> LENGTH: 20
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (20)..(20)
<223> OTHER INFORMATION: dideoxynucleotide

<400> SEQUENCE: 19
cctgcttggg aacttgaggg                                       20

<210> SEQ ID NO 20
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 20
tgcttgggaa cttgaggg                                         18

<210> SEQ ID NO 21
<211> LENGTH: 26
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (26)..(26)
<223> OTHER INFORMATION: dideoxynucleotide

<400> SEQUENCE: 21
tgactgaccc ctattccctg cttagg                                26

<210> SEQ ID NO 22
<211> LENGTH: 22
<212> TYPE: DNA
```

```
<213> ORGANISM: Artificial Sequence
<220> FEATURE:
<223> OTHER INFORMATION: oligonucleotide
<221> NAME/KEY: misc_feature
<222> LOCATION: (22)..(22)
<223> OTHER INFORMATION: dideoxynucleotide

<400> SEQUENCE: 22
tgacccctat tccctgctta gg                                    22

<210> SEQ ID NO 23
<211> LENGTH: 20
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (20)..(20)
<223> OTHER INFORMATION: dideoxynucleotide

<400> SEQUENCE: 23
acccctattc cctgcttagg                                       20

<210> SEQ ID NO 24
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 24
ccctattccc tgcttagg                                         18

<210> SEQ ID NO 25
<211> LENGTH: 26
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (26)..(26)
<223> OTHER INFORMATION: dideoxynucleotide

<400> SEQUENCE: 25
tgactgaccc ctattcgctg cttagg                                26

<210> SEQ ID NO 26
<211> LENGTH: 22
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (22)..(22)
<223> OTHER INFORMATION: dideoxynucleotide

<400> SEQUENCE: 26
tgacccctat tcgctgctta gg                                    22

<210> SEQ ID NO 27
<211> LENGTH: 20
<212> TYPE: DNA
<213> ORGANISM: Artificial Sequence
<220> FEATURE:
<223> OTHER INFORMATION: oligonucleotide
<221> NAME/KEY: misc_feature
```

<222> LOCATION: (20)..(20)
<223> OTHER INFORMATION: dideoxynucleotide

<400> SEQUENCE: 27
acccctattc gctgcttagg					20

<210> SEQ ID NO 28
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 28
ccctattcgc tgcttagg					18

<210> SEQ ID NO 29
<211> LENGTH: 26
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (26)..(26)
<223> OTHER INFORMATION: dideoxynucleotide

<400> SEQUENCE: 29
tgactgaccc ttattccctg cttagg					26

<210> SEQ ID NO 30
<211> LENGTH: 22
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (22)..(22)
<223> OTHER INFORMATION: dideoxynucleotide

<400> SEQUENCE: 30
tgacccttat tccctgctta gg					22

<210> SEQ ID NO 31
<211> LENGTH: 20
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (20)..(20)
<223> OTHER INFORMATION: dideoxynucleotide

<400> SEQUENCE: 31
acccttattc cctgcttagg					20

<210> SEQ ID NO 32
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 32
ccttattccc tgcttagg                                                18

<210> SEQ ID NO 33
<211> LENGTH: 40
<212> TYPE: DNA
<213> ORGANISM: Homo sapiens

<400> SEQUENCE: 33
gactgacccc tattccctgc ttrggaactt gagggtgtc                         40

<210> SEQ ID NO 34
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 34 accctattc cctgctta                                                 18

<210> SEQ ID NO 35
<211> LENGTH: 17
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 35
ttccctgctt gggaact                                                 17

<210> SEQ ID NO 36
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 36
ccctgcttgg gaacttga                                                18

<210> SEQ ID NO 37
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 37
tgcttgggaa cttgaggg                                                18

<210> SEQ ID NO 38
<211> LENGTH: 18
<212> TYPE: DNA
<213> ORGANISM: Artificial Sequence
<220> FEATURE:

```
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 38
acccctattc cctgattg                                                 18

<210> SEQ ID NO 39
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 39
acccctattc cgtgcttg                                                 18

<210> SEQ ID NO 40
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 40
acccctatcc cctgcttg                                                 18

<210> SEQ ID NO 41
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 41
accccgattc cctgcttg                                                 18

<210> SEQ ID NO 42
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (18)..(18)
<223> OTHER INFORMATION: dideoxynucleotide

<400> SEQUENCE: 42
actcctattc cctgcttg                                                 18

<210> SEQ ID NO 43
<211> LENGTH: 25
<212> TYPE: DNA
<213> ORGANISM: Homo sapiens

<400> SEQUENCE: 43
tctgactgac ccctattccc tgctt                                         25
```

```
<210> SEQ ID NO 44
<211> LENGTH: 24
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (24)..(24)
<223> OTHER INFORMATION: dideoxynucleotide

<400> SEQUENCE: 44
tgactgaccc ctattccctg ctta                                          24

<210> SEQ ID NO 45
<211> LENGTH: 26
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (26)..(26)
<223> OTHER INFORMATION: dideoxynucleotide

<400> SEQUENCE: 45
tctgactgac ccctattccc tgcttg                                        26

<210> SEQ ID NO 46
<211> LENGTH: 24
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (24)..(24)
<223> OTHER INFORMATION: dideoxynucleotide

<400> SEQUENCE: 46
actgacccct attccctgct tggg                                          24

<210> SEQ ID NO 47
<211> LENGTH: 26
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (26)..(26)
<223> OTHER INFORMATION: dideoxynucleotide

<400> SEQUENCE: 47
taggaacttg gggggtgtca gagccc                                        26
```